United States Patent
Dasgupta et al.

(10) Patent No.: US 10,023,965 B2
(45) Date of Patent: Jul. 17, 2018

(54) ELECTROLYTIC BUFFER GENERATOR

(75) Inventors: Purnendu K. Dasgupta, Arlington, TX (US); Yongjing Chen, Sunnyvale, CA (US); Kannan Srinivasan, Tracy, CA (US)

(73) Assignees: Board of Regents, The University of Texas System, Austin, TX (US); Dionex Corporation, Sunnyvale, CA (US)

( * ) Notice: Subject to any disclaimer, the term of this patent is extended or adjusted under 35 U.S.C. 154(b) by 534 days.

(21) Appl. No.: 13/593,426

(22) Filed: Aug. 23, 2012

(65) Prior Publication Data

US 2013/0220814 A1 Aug. 29, 2013

Related U.S. Application Data

(60) Provisional application No. 61/528,127, filed on Aug. 26, 2011, provisional application No. 61/526,592, filed on Aug. 23, 2011.

(51) Int. Cl.
| | | |
|---|---|---|
| *B01D 61/44* | (2006.01) | |
| *C25B 7/00* | (2006.01) | |
| *B01D 61/46* | (2006.01) | |
| *B01D 15/16* | (2006.01) | |
| *G01N 30/34* | (2006.01) | |

(52) U.S. Cl.
CPC .............. *C25B 7/00* (2013.01); *B01D 15/168* (2013.01); *B01D 61/44* (2013.01); *B01D 61/445* (2013.01); *B01D 61/46* (2013.01); *G01N 30/34* (2013.01)

(58) Field of Classification Search
CPC .... B01D 61/422; B01D 61/44; B01D 61/445; B01D 61/46; G01N 30/26; G01N 30/28; G01N 30/285; G01N 30/34; G01N 30/347; G01N 30/36; G01N 2030/342; G01N 2030/347
See application file for complete search history.

(56) References Cited

U.S. PATENT DOCUMENTS

| | | | |
|---|---|---|---|
| 3,239,442 A | 3/1966 | Tirrell | |
| 3,341,299 A * | 9/1967 | Catravas | ........................ 436/89 |
| 4,459,357 A | 7/1984 | Jansen et al. | |

(Continued)

FOREIGN PATENT DOCUMENTS

| | | |
|---|---|---|
| EP | 1897601 A1 | 12/2008 |
| KR | 10-2005-0020298 | 3/2005 |

(Continued)

OTHER PUBLICATIONS

Page 207 of a faculty publication of the National Cheng Kung University, published in 1983.*

(Continued)

*Primary Examiner* — Brian W Cohen
*Assistant Examiner* — Salil Jain
(74) *Attorney, Agent, or Firm* — Morgan, Lewis & Bockius LLP

(57) ABSTRACT

Buffer generators are described based on electrodialytic devices. The methods of using these devices can generate buffers for diverse applications, including separations, e.g., HPLC and ion chromatography. Also provided are chromatographic devices including the buffer generators, generally located upstream from a chromatography column, sample injector valve or both.

5 Claims, 23 Drawing Sheets

(56) References Cited

U.S. PATENT DOCUMENTS

| | | | |
|---|---|---|---|
| 4,671,863 A | 6/1987 | Tejeda | |
| 4,936,962 A * | 6/1990 | Hatzidimitriu | 426/239 |
| 4,999,098 A | 3/1991 | Pohl | |
| 5,045,204 A * | 9/1991 | Dasgupta | B01D 19/0031 204/257 |
| 5,200,046 A * | 4/1993 | Chlanda | B01D 61/445 204/534 |
| 5,316,680 A * | 5/1994 | Frechet et al. | 210/635 |
| 5,730,867 A * | 3/1998 | Drew et al. | 210/198.2 |
| 2003/0132163 A1* | 7/2003 | Srinivasan et al. | 210/656 |
| 2004/0149581 A1 | 8/2004 | Srinivasan et al. | |
| 2004/0195100 A1 | 10/2004 | Srinivasan et al. | |
| 2005/0082228 A1* | 4/2005 | De Lamotte | B01D 15/166 210/656 |
| 2006/0266650 A1* | 11/2006 | Han | B01D 61/422 204/518 |
| 2009/0178928 A1 | 7/2009 | Groos et al. | |
| 2012/0031763 A1 | 2/2012 | Ohmi et al. | |

FOREIGN PATENT DOCUMENTS

| | | |
|---|---|---|
| WO | 9951529 | 10/1999 |
| WO | 2010019402 A1 | 2/2010 |
| WO | WO 2010/122989 A1 | 10/2010 |
| WO | WO 2011/037530 A1 | 3/2011 |
| WO | 2012073566 A1 | 6/2012 |

OTHER PUBLICATIONS

Chen et al., Electrodialytic Membrane Suppressors for Ion Chromatography Make Programmable Buffer Generators, Anal. Chem., 2012, 84, 67-75 and 12 pages of supporting information and 24 pages Excel spreadsheet.

Chen et al., pH- and Concentration-Programmable Electrodialytic Buffer Generator, Anal. Chem., 2012, 84, 59-66 and 22 pages of supporting information.

Ohira et al., Electrodialytic Ion Isolation for Matrix Removal, Anal. Chem., 2012, 84, 5421-5426.

Kielland et al., Individual Activity Coefficients of Ions in Aqueous Solutions, J. Amer. Chem. Soc., 1937, 59, 1675-1678.

* cited by examiner

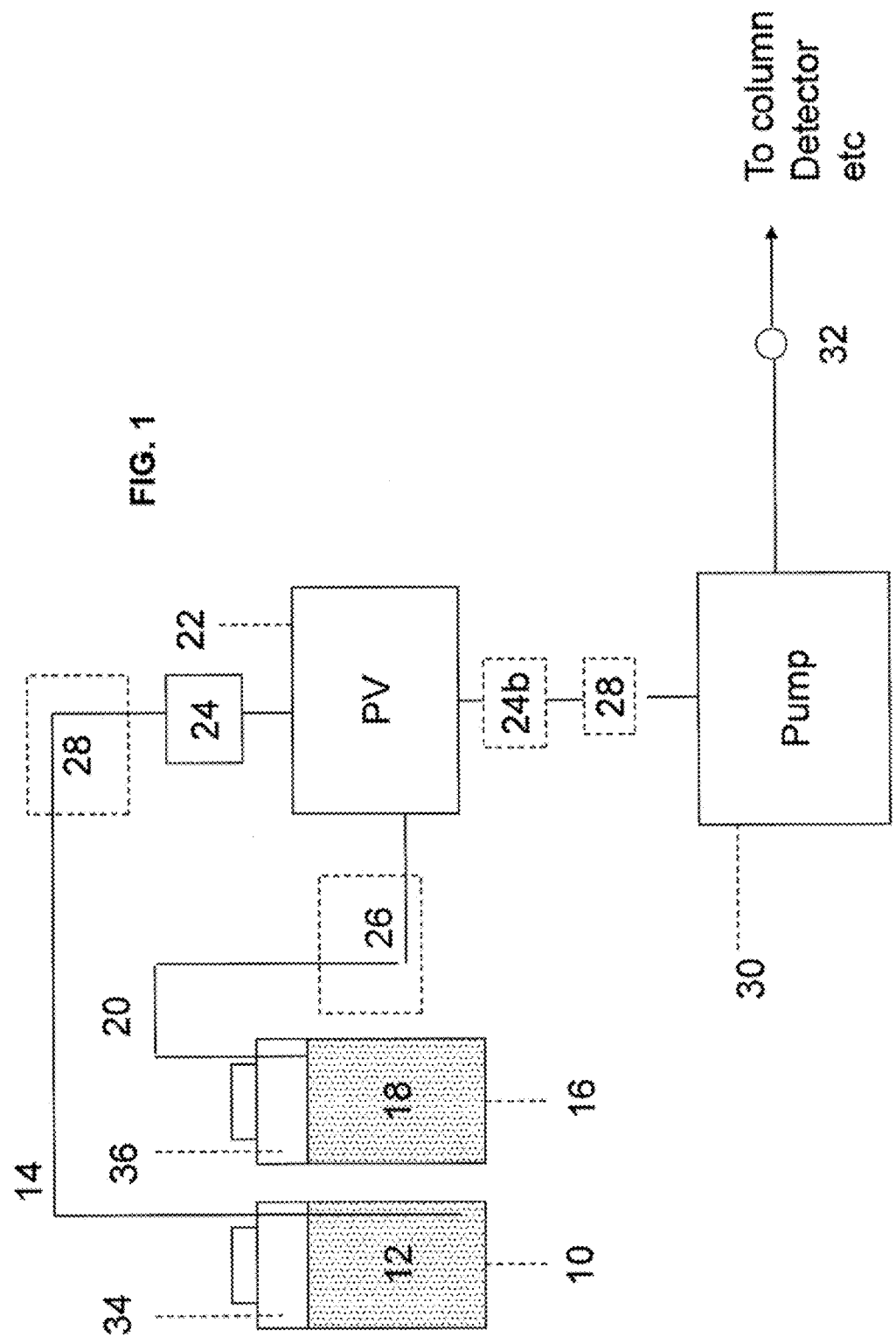

(a) 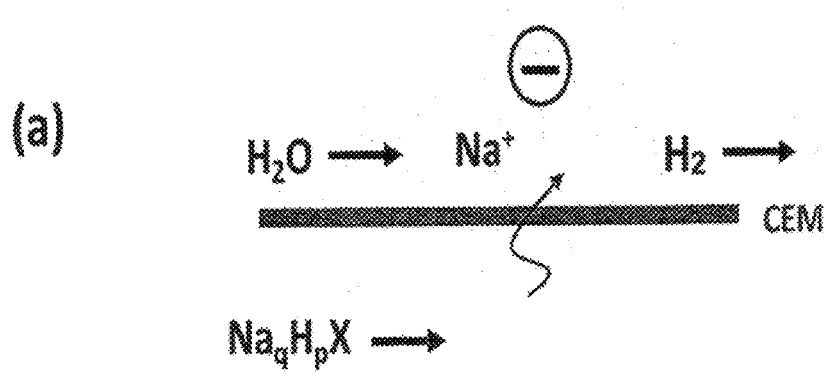
FIG. 2A
(b) 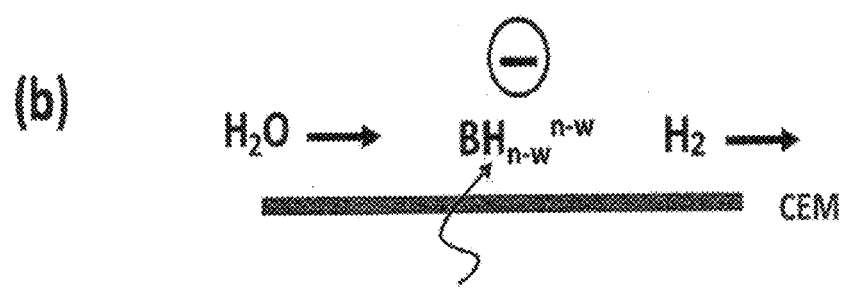

FIGURE 14

Table 1. Conductance Values for Current Steps in Figure 7

| 0 mA, A* | | 40 mA, A | | 40 mA, D* | | 80 mA, A | | 80 mA, D | | 120 mA, D | | 120 mA, D | | 160 mA, D | |
|---|---|---|---|---|---|---|---|---|---|---|---|---|---|---|---|
| t, min | Cond mS/cm | t, min | Cond mS/cm | t, min | Cond mS/cm | t, min | Cond mS/cm | t, min | Cond mS/cm | t, min | Cond mS/cm | t, min | Cond mS/cm | t, min | Cond mS/cm |
| 45.00 | 18.15 | 10.00 | 15.87 | 40.00 | 15.51 | 15.00 | 13.63 | 35.00 | 13.39 | 20.00 | 11.37 | 30.00 | 11.22 | 25.00 | 8.99 |
| 85.00 | 18.12 | 50.00 | 15.93 | 80.00 | 15.51 | 55.00 | 13.68 | 75.00 | 13.43 | 60.00 | 11.43 | 70.00 | 11.28 | 65.00 | 9.05 |
| 125.0 | 18.25 | 90.00 | 15.93 | 120.00 | 15.59 | 95.00 | 13.70 | 115.00 | 13.47 | 100.00 | 11.43 | 110.00 | 11.30 | 105.00 | 9.07 |
| 165.0 | 18.19 | 130.00 | 16.00 | 160.00 | 15.58 | 135.00 | 13.74 | 155.00 | 13.51 | 140.00 | 11.47 | 150.00 | 11.34 | 145.00 | 9.11 |
| mean | 18.18 | | 15.93 | | 15.55 | | 13.69 | | 13.45 | | 11.42 | | 11.29 | | 11.29 |
| sd | 0.06 | | 0.06 | | 0.05 | | 0.05 | | 0.05 | | 0.04 | | 0.05 | | 0.05 |
| %Rsd | 0.31 | | 0.35 | | 0.29 | | 0.33 | | 0.36 | | 0.36 | | 0.43 | | 0.43 |
| | | | | %diff | | Diff | 0.38 | %diff | | diff | 0.24 | %diff | | diff | 0.14 |
| | | | | | | | 1.22 | | | | 0.88 | | | | 0.61 |

* A indicates ascending step, D indicates descending step.

FIGURE 15

Table 2. pH Values for Current Steps in Figure 7

| 0 mA, A* | | 40 mA, A | | 40 mA, D* | | 80 mA, A | | 80 mA, D | | 120 mA, A | | 120 mA, D | | 160 mA, D | |
|---|---|---|---|---|---|---|---|---|---|---|---|---|---|---|---|
| t, min | pH | t, min | pH | t, min | pH | t, min | pH | t, min | pH | t, min | pH | t, min | pH | t, min | pH mS/cm |
| 45.00 | 11.91 | 10.00 | 11.62 | 40.00 | 11.51 | 15.00 | 10.94 | 35.00 | 10.80 | 20.00 | 7.62 | 30.00 | 7.54 | 25.00 | 6.78 |
| 85.00 | 11.91 | 50.00 | 11.58 | 80.00 | 11.51 | 55.00 | 10.91 | 75.00 | 10.80 | 60.00 | 7.60 | 70.00 | 7.54 | 65.00 | 6.78 |
| 125.00 | 11.91 | 90.00 | 11.57 | 120.00 | 11.52 | 95.00 | 10.90 | 115.00 | 10.82 | 100.00 | 7.61 | 110.00 | 7.57 | 105.00 | 6.81 |
| 165.00 | 11.92 | 130.00 | 11.58 | 160.00 | 11.54 | 135.00 | 10.91 | 155.00 | 10.84 | 140.00 | 7.64 | 150.00 | 7.61 | 145.00 | 6.87 |
| mean | 11.91 | | 11.59 | | 11.52 | | 10.91 | | 10.81 | | 7.62 | | 7.57 | | 6.81 |
| sd | 0.01 | | 0.02 | | 0.01 | | 0.02 | | 0.02 | | 0.02 | | 0.03 | | 0.05 |
| %Rsd | 0.04 | | 0.19 | | 0.12 | | 0.16 | | 0.17 | | 0.21 | | 0.40 | | 0.67 |
| | | | | difference 0.07 | | | | difference 0.10 | | | | difference 0.05 | | | |

* A indicates ascending step, D indicates descending step.

FIGURE 16

Table 3. Conductance Values for Small Current Steps, Figure 13

| 100 mA, A | | 102 mA, A | | 102 mA, D | | 104 mA, A | | 104 mA, D | | 106 mA, A | | 106 mA, D | | 108 mA, D | |
|---|---|---|---|---|---|---|---|---|---|---|---|---|---|---|---|
| t, min | Cond mS/cm | t, min | Cond mS/cm | t, min | Cond mS/cm | t, min | Cond mS/cm | t, min | Cond mS/cm | t, min | Cond mS/cm | t, min | Cond mS/cm | t, min | Cond mS/cm |
| 45.00 | 12.32 | 10.00 | 12.13 | 40.00 | 12.19 | 15.00 | 12.02 | 35.00 | 12.07 | 20.00 | 11.93 | 30.00 | 11.95 | 25.00 | 11.83 |
| 85.00 | 12.38 | 50.00 | 12.22 | 80.00 | 12.24 | 55.00 | 12.11 | 75.00 | 12.12 | 60.00 | 11.99 | 70.00 | 12.00 | 65.00 | 11.88 |
| 125.00 | 12.39 | 90.00 | 12.25 | 120.00 | 12.25 | 95.00 | 12.15 | 115.00 | 12.12 | 100.00 | 12.03 | 110.00 | 12.01 | 105.00 | 11.91 |
| 165.00 | 12.39 | 130.00 | 12.28 | 160.00 | 12.28 | 135.00 | 12.18 | 155.00 | 12.16 | 140.00 | 12.08 | 150.00 | 12.06 | 145.00 | 11.96 |
| mean | 12.37 | | 12.22 | | 12.24 | | 12.12 | | 12.12 | | 12.01 | | 12.00 | | 11.89 |
| sd | 0.03 | | 0.06 | | 0.04 | | 0.07 | | 0.04 | | 0.06 | | 0.05 | | 0.05 |
| %Rsd | 0.27 | | 0.53 | | 0.30 | | 0.60 | | 0.33 | | 0.54 | | 0.41 | | 0.46 |

Differences in ascending and descending steps within measurement uncertainty

* A indicates ascending step, D indicates descending step.

FIGURE 17

Table 4. pH Values for Small Current Steps, Figure 13

| 100 mA, A t, min | pH | 102 mA, A t, min | pH | 102 mA, D t, min | pH | 104 mA, A t, min | pH | 104 mA, D t, min | pH | 106 mA, A t, min | pH | 106 mA, D t, min | pH | 108 mA, D t, min | pH |
|---|---|---|---|---|---|---|---|---|---|---|---|---|---|---|---|
| 45.00 | 9.37 | 10.00 | 9.03 | 40.00 | 8.97 | 15.00 | 8.58 | 35.00 | 8.55 | 20.00 | 8.25 | 30.00 | 8.24 | 25.00 | 8.07 |
| 85.00 | 9.38 | 50.00 | 9.03 | 80.00 | 8.98 | 55.00 | 8.60 | 75.00 | 8.56 | 60.00 | 8.27 | 70.00 | 8.25 | 65.00 | 8.07 |
| 125.00 | 9.38 | 90.00 | 9.02 | 120.00 | 8.97 | 95.00 | 8.59 | 115.00 | 8.55 | 100.00 | 8.26 | 110.00 | 8.24 | 105.00 | 8.07 |
| 165.00 | 9.37 | 130.00 | 9.03 | 160.00 | 8.99 | 135.00 | 8.59 | 155.00 | 8.57 | 140.00 | 8.27 | 150.00 | 8.24 | 145.00 | 8.07 |
| Mean | 9.38 | | 9.03 | | 8.98 | | 8.59 | | 8.56 | | 8.26 | | 8.24 | | 8.07 |
| Sd | 0.00 | | 0.01 | | 0.01 | | 0.01 | | 0.01 | | 0.01 | | 0.00 | | 0.00 |
| %Rsd | 0.04 | | 0.07 | | 0.14 | | 0.09 | | 0.12 | | 0.10 | | 0.04 | | 0.02 |

Green pH electrode response times, the difference between ascending and descending steps are likely not significant.

* A indicates ascending step, D indicates descending step

ELECTROLYTIC BUFFER GENERATOR

CROSS-REFERENCE TO RELATED APPLICATIONS

This application claims the priority benefit under 35 U.S.C. § 119(e) of U.S. Provisional Patent Application Ser. No. 61/526,592 by Purnendu K. Dasgupta, Yongjing Chen, and Kannan Srinivasan for "Three-Electrode Buffer Generator and Method" filed Aug. 23, 2011; and U.S. Provisional Patent Application Ser. No. 61/528,127 by Purnendu K. Dasgupta, Yongjing Chen, and Kannan Srinivasan for "Membrane Suppressor Buffer Generator" filed Aug. 26, 2011, the entire disclosure of which is incorporated by reference.

BACKGROUND

Buffers are widely used for pH control of chemical processes. A buffered solution resists changes in pH when acids or bases are added or when dilution occurs. Biochemists are particularly concerned with buffers because the proper functioning of any biological system depends on pH. The rate of one particular enzyme-catalyzed reaction varies with pH. For an organism to survive, pH of each subcellular compartment has to be precisely controlled so that each reaction proceeds at the proper rate. The majority of biological samples that are used in research are made in buffers, such as phosphate, Tris-HCl at pH around 7.

Microbial fuel cells (MFCs), which can directly generate electricity from biodegradable substance, have rapidly gained increasing research attention. Microbes oxidize organic substrates to supply electrons to the anode; the electrons then travel through an external circuit to the cathode and participate in reduction reactions. Associated with these reactions is the generation of $H^+$ and $OH^-$ from water electrolysis in the anolyte and catholyte, respectively, which creates a pH imbalance in system. Since the pH imbalance produces a 0.059 V/pH potential loss, minimizing the pH imbalance is necessary for maximizing the power densities. Phosphate buffers are usually used to stabilize the pH and reduce the internal resistance, which in turn enhances the system performance. In order to have a sufficient supply of protons in a cathode compartment, a high concentration of buffer is needed, and over the time it might still become depleted. A stable supply of fresh buffer will be attractive.

Buffers are of wide utility in analytical chemistry as well. Reversed-phase high performance liquid chromatography (RP-HPLC) has always been a very powerful tool for organic compound analysis, especially biological sample analysis. Buffers like phosphate or acetate are widely employed in the mobile phase in the analysis of ionizable compounds. Because the retention of ionizable acid/base compounds has a strong dependence of their degree of ionization, a correctly chosen buffer pH will ensure that the ionizable functional group is in a single form, whether ionic or neutral. When developing a rugged method, it is desirable to select a mobile phase with a final pH at least one pH unit away from any analyte's pK value to cause ionization or suppression of the analytes. Slight variations in pH can have a dramatic impact on separation, in terms of selectivity, capacity factor, peak shape, resolution and reproducibility. An improper pH for ionizable analytes often leads to asymmetric peaks that are broad, tail, split or shoulder. And sharp, symmetrical peaks are necessary in quantitative analysis in order to achieve low detection limits, low relative standard deviations between injections, and reproducible retention times. Even in the analysis of non-ionizable compounds, it is often equally important to control pH when working with field samples in the presence of ionizable contaminants or impurities so as to eliminate the interference of undesirable peaks. If the sample solution is at a pH damaging to the column, the buffer will quickly bring the pH of the injected solution to a less harmful pH. Another technique of RP-HPLC, ion-pair chromatography (IPC) also requires precise control of pH in the mobile phase, because variation of pH in the mobile phase can introduce large changes in the degree of ionization of not only the solutes but also the ion-pairing reagent. In practice, a chromatographer usually measure the pH of the buffer additives before mixing it with other solvents, but the pKa values of the acids used to prepare the buffers change with the solvent composition (and each in a different degree), and so does the pH of the buffer. Sometimes, the pH is measured after mixing the buffer with the organic modifier; even in this instance, the potentiometric system is usually calibrated with aqueous standards, and the measured pH is not the true pH of the mobile phase. Theoretically, a chromatographer can estimate the concentration of buffer needed to achieve a desired pH for separation based on calculation from equations. However, in reality pH can vary significantly from those calculations. Therefore the analyst has to experimentally determine and report the value for the mobile phase pH with a calibrated pH meter to ensure reproducibility results. When developing a method, the analyst might have to adjust the mobile phase many times before it reaches the optimum condition. With one stock buffer solution, the final concentration of buffer can only be varied by varying the ratio of buffer to the organic solvent, which largely limits the flexibility of the optimization process. To make different buffer stock solutions is tedious and time-consuming. If the buffer concentration can be varied simply by varying the applied current, it will provide a much efficient way and reduce lots of waste solvents.

pH-based separation of proteins with ion-exchange chromatography is another chromatographic technique that relies on buffers. Initially it employs nearly linear pH gradients generated from mobile phase (ampholyte buffers) and stationary phase (weak anion-exchange column) to elute proteins in the order of their pI, and was termed "chromatofocusing". More recently, the technique was developed into "gradient chromatofocusing", which employs common buffers with low molecular mass instead of polymeric ampholytes. There are two types of gradients; a pH gradient in time at column outlet causing differential elution of proteins and a pH gradient in distance within the column affecting the focusing of the protein bands. HPLC gradient pumps are typically used to generate the linear pH gradient in time by varying the ratio of high-pH buffer and low-pH buffer, which are mixtures of buffer components with pKa values approximately equally spaced throughout the gradient pH range.

Capillary electrophoresis (CE) is another powerful separation tool for analysis of proteins and peptides, as well as drug enantiomers. Its unprecedented resolution allowing separation of species with very subtle differences in structure is a consequence of its extremely high efficiency, which, to some extent, depends on the running buffers it employs. Manipulation of buffer pH is usually a key strategy to optimize a separation, since buffer pH not only determines the extent of ionization of each individual analyte, but also strongly influences the charge of the capillary wall surface and the zeta potential, consequently affects both electrophoretic and electroosmotic velocities. Electrolysis of water is one of the most significant reactions occurring at the inlet and outlet vials in a CE experiment, the resulting H+ and OH− can change the pH in the vials. Thus, to successfully maintain the pH of the buffer, large vials should be used and the buffer must have adequate buffering capacity to neutralize the H+ and OH− produced, and the buffer vials should be replenished regularly. By manipulating the running buffers, sample pre-concentration can also be achieved to overcome the drawback of limited sensitivity in CE.

Essentially a buffer is a mixture of an acid and its conjugate base. There must be comparable amounts of the conjugate acid and base (say, within a factor of 10) to exert significant buffering. The most common way to prepare a buffer solution is to decide the ratio of the conjugate acid-base pair based on Henderson-Hasselbalch equation, and weigh out the two components separately to obtain the desired ratio and then dissolve in water. An alternative is to weigh out one of the component, and produce the other component by a specified amount of strong acid or strong base to yield the desired ratio. Although it is a common practice to adjust pH of certain buffer solution with concentrated strong acid or base, it is easy to overshoot by adding too much of the titrants and have to make another solution and start over again.

Improved devices and methods of generating buffers, which provided reproducible generation of ions across a range of currents and/or pH values would greatly simplify practices in which buffers are a key component, for example, ion chromatography. By harnessing the power and versatility of ion suppression technology, Applicant believes that improved devices and methods to generate buffers of consistent concentration and pH can be developed.

SUMMARY

When pursuing ion chromatography, the suppressor is normally placed after the separation column and before the detector. The purpose of the suppressor is to convert the eluent to a weakly conductive species while maximizing the analyte conductivity particularly for fully dissociated species. The suppressor can also be used for suppressing the contribution from the sample such as when analyzing anions in base. The role of the suppressor during anion analysis is to completely remove the sample cations and convert in this case the sample matrix to water while converting the analyte anions to acids. The electrolytic suppressor in the above application cannot be operated continuously in a partially suppressed mode since it would be difficult for a given current to maintain a partially suppressed status and the residual static capacity in the suppressor would be depleted over time due to the influx of ions from the eluent or sample as the case may be. Further such a device would never produce reproducible response for the analyte ions since at some point in time the outlet of the device would be in the eluent cation form. The analyte would then be converted to a mixture of acid and salt form resulting in variances in response. Hence traditionally the commercial suppressor has always been operated with a slight excess current to ensure a reservoir of static capacity.

A buffer generator on the other hand is not restricted by the capacity depletion effects if the configuration as described herein is maintained. Further the buffer generator resists changes in the pH, therefore, by adjusting the conditions within the suppressor, it is possible to achieve pH programmable buffer generation.

Thus, in an exemplary embodiment, the invention provides an electrodialytic method for generating a modified buffer solution. The method includes:

(a) flowing a buffer solution, including cations and anions, at a concentration greater than about 10 mM through a modified-buffer generation flow channel under a pressure less than about 30 psi, the modified-buffer generation flow channel including a first electrode disposed therein;

(b) flowing an aqueous liquid stream through a first ion-receiving flow channel including a second electrode disposed therein. The ion-receiving flow channel is separated from the modified-buffer generation flow channel by an ion exchange barrier including exchangeable cations or anions, but not both. The barrier is capable of blocking bulk liquid flow. In an exemplary embodiment, the membrane has a surface area greater than about 0.5 in$^2$.

The method of the invention further includes, (c) passing a current between the first and second electrodes across the modified-buffer flow generation channel and the ion-receiving flow channel to cause the cations or anions, but not both, to be transported from the modified-buffer flow channel across the first ion exchange barrier into the ion-receiving flow channel to generate a modified buffer solution which exits from the modified-buffer generation flow channel. The cations or anions can be transported from the modified-buffer flow channel across the first ion exchange barrier into the ion-receiving channel.

The method may also include flowing an aqueous liquid stream through a source channel for ions separated by a second ion exchange membrane from the modified-buffer flow channel, the second ion exchange membrane including exchangeable ions of the same charge, positive or negative, as the exchangeable ions of the first ion exchange membrane. The ions are a member selected from hydronium ions and hydroxide ions.

In another embodiment of the method, first electrode can be disposed in the ion-receiving channel and the second electrode is disposed in the source channel. The method may also include injecting a sample with analyte ions to be separated into the exiting modified buffer and separating the analytes; the buffer solution flowing to the modified-buffer flow channel not being previously generated by an electrolytic eluent generator. In an embodiment, cations or anions can be transported from the modified-buffer channel into a member selected from the ion-receiving channel and the source channel. The method may also include outputting the modified buffer solution from the modified-buffer generation flow channel with a modified buffer concentration, in which a magnitude of the current is proportional to a change in a concentration of the flowed buffer solution.

The method may also include flowing an aqueous liquid stream through an electrode channel for ions separated by a bipolar membrane from the modified-buffer flow channel, the bipolar membrane configured to split water and generate hydronium ions and hydroxide ions, and also to block bulk liquid flow, the current passing between the first electrode disposed in the electrode chamber and the second electrode disposed in the ion-receiving channel via the modified-buffer flow generation channel. The ions may be either hydronium ions or hydroxide ions.

In various embodiments, the invention provides an electrodialytic method for generating a modified buffer solution. An exemplary method includes:

(a) flowing a buffer solution, including cations and anions through a modified-buffer generation flow channel. The modified-buffer generation flow channel is separated from a first ion-receiving flow channel by an anion exchange membrane capable of blocking bulk liquid flow. The modified-buffer generation flow channel is separated from a second ion-receiving flow channel by a cation exchange membrane capable of blocking bulk liquid flow;

(b) flowing an aqueous liquid stream through the first and second ion-receiving flow channels separated from the modified-buffer flow channel; and (c) passing a current between first and second electrodes across the modified-buffer flow generation channel and at least one ion-receiving flow channel to cause cations or anions to be transported across a member selected from the anion exchange membrane and the cation exchange membrane into a member selected from the first ion-receiving flow channel and the second ion-receiving flow channel, respectively, thereby generating a modified buffer solution which exits from the modified-buffer generation flow channel. In an exemplary embodiment, the first and second electrodes are disposed within the first and second ion receiving flow channel, respectively.

In various embodiments, the invention provides an electrodialytic method for generating a modified buffer solution. The method includes:

(a) flowing an acid or base solution, including cations and anions through a modified-buffer generation flow channel;

(b) flowing an aqueous liquid stream through a first ion-receiving flow channel separated from the modified-buffer flow channel by a first ion exchange barrier including exchangeable cations or anions, but not both, and capable of blocking bulk liquid flow; and (c) passing a current between first and second electrodes across the modified-buffer flow generation channel and the first ion-receiving flow channel to cause the cations or anions, but not both, to be transported from the modified-buffer flow channel across the first ion exchange barrier into the first ion-receiving flow channel to generate a modified buffer solution which exits from the modified-buffer generation flow channel.

In an exemplary embodiment, the method further includes flowing an aqueous liquid stream through a second ion-receiving flow channel separated from the modified-buffer flow channel by a second ion exchange barrier including exchangeable cations or anions, but not both, and capable of blocking bulk liquid flow. The first and second electrodes are disposed within the first and second ion receiving flow channel, respectively. In an exemplary embodiment, the first and second electrode are disposed within the first or second ion receiving flow channel and the modified-buffer generation channel, respectively.

In an exemplary embodiment, the invention provides an electrodialytic buffer generator including:

(a) a flow-through central modified buffer-generating channel having an inlet and an outlet;

(b) a second channel including a first electrode, the channel having an inlet and an outlet;

(c) a third channel including a second electrode, the channel having an inlet and an outlet;

(d) a cation exchange barrier, capable of passing cations but not anions and of blocking bulk liquid flow, disposed between the first channel and the buffer-generating channel;

(e) an anion exchange barrier, capable of passing anions but not cations and of blocking bulk liquid flow, disposed between the third channel and the buffer-generating channel; and (f) a first current source connected to the first and second electrodes The present invention provides a buffer generator with novel features. Exemplary buffer generators of the invention operate at low pressure. Some of the benefits of a low pressure generator include: a) inline adjustment of the pH is feasible; b) multiple electrolytes can be premixed using the proportioning valve make the technique automated and adding to the ease of use from an implementation perspective; c) the cost of designing a low pressure device is significantly lower than high pressure modules; and d) it is feasible to mix with electroactive solvents post generator by using a proportioning valve format. Implementing this configuration in the high pressure format is only feasible with an additional high pressure pump. It should be noted that the HPLC instrument pressure specifications and operability under high pressure conditions have been on the rise for the past decade and the above low pressure configuration as per the present invention minimizes any high pressure development projects thus simplifying the product/product development costs.

An additional advantage is the buffer generators provided herein are not restricted by capacity depletion effects.

In the embodiments below, an ion-receiving channel, source channel, or ion source channel may be replaced with a chamber format. In such a case, a liquid within the chamber can be substantially non-flowing and static.

An electrodialytic method for generating a modified buffer solution can include flowing a buffer solution, including cations and anions through a modified-buffer generation flow channel, wherein the modified-buffer generation flow channel is separated from a first ion-receiving chamber by an anion exchange membrane capable of blocking bulk liquid flow and wherein the modified-buffer generation flow channel is separated from a second ion-receiving chamber by a cation exchange membrane capable of blocking bulk liquid flow; passing a current between first and second electrodes across the ion-receiving chamber to cause cations to be transported across a cation exchange membrane and to cause anions to be transported across an anion exchange membrane, wherein the first and second electrodes are disposed within the first and second ion-receiving chambers, respectively, and are separated from the modified-buffer flow channel, thereby generating a modified buffer solution which exits from the modified-buffer generation flow channel. The current can be passed across the modified buffer flow generation channel from the first ion-receiving chamber to the second ion receiving chamber. Either cations or anions can be transported from the modified-buffer channel into either the first ion-receiving chamber or the second ion-receiving chamber. Alternatively either cations or anions can be transported into the modified-buffer channel from either the first ion-receiving chamber or the second ion-receiving chamber. The method may also include outputting the modified buffer solution from the modified-buffer generation flow channel with a modified buffer concentration, in which a magnitude of the current is proportional to a change in a concentration of the flowed buffer solution. Either cations or anions can flow from the ion-receiving chamber. The method may further include injecting a sample with analyte ions to be separated into the exiting modified buffer and separating the analytes. The buffer solution flowing to the modified-buffer flow channel was not previously generated by an electrolytic eluent generator.

An electrodialytic method for generating a modified buffer solution includes flowing an aqueous liquid stream through a modified-buffer generation flow channel; passing a current between first and second electrodes across the modified-buffer flow generation channel and a first ion-receiving chamber to cause cations or anions, but not both, to be transported across the first ion exchange barrier to generate a modified buffer solution which exits from the modified-buffer generation flow channel, the first ion-receiving chamber being separated from the modified-buffer flow channel by the first ion exchange barrier including exchangeable cations or anions, but not both, and capable of blocking bulk liquid flow. The aqueous liquid stream may include an acid or base solution that includes cations and anions. The acid or base solution may be at a concentration greater than about 10 mM. Either cations or anions can be transported from the modified-buffer flow channel across the first ion exchange barrier into the ion receiving chamber. A second ion-receiving chamber can be separated from the modified-buffer flow channel by a second ion exchange barrier including exchangeable cations or anions, but not both, and capable of blocking bulk liquid flow, the current passing between the first electrode disposed in the first ion-receiving chamber and the second electrode disposed in the second ion-receiving chamber via the modified-buffer flow generation chamber. Either cations or anions can be transported into the modified-buffer channel from a member selected from the first ion-receiving chamber and the second ion-receiving chamber. The method may also include outputting the modified buffer solution from the modified-buffer generation flow channel with a modified buffer concentration, in which a magnitude of the current is proportional to a change in a concentration of the flowed acid or base solution. Either cations or anions can flow from the ion-receiving chamber. The method may further include injecting a sample with analyte ions to be separated into the exiting modified buffer and separating the analytes; the buffer solution flowing to the modified-buffer flow channel not being previously generated by an electrolytic eluent generator.

In another embodiment, the electrode chamber for ions may be separated by a bipolar membrane from the modified-buffer flow channel, the bipolar membrane configured to split water and generate hydronium ions and hydroxide ions, and also to block bulk liquid flow, the current passing between the first electrode disposed in the electrode chamber and the second electrode disposed in the first ion-receiving chamber via the modified-buffer flow generation channel. Either cations or anions can be transported from the modified-buffer generation flow channel into the first ion-receiving chamber.

An electrodialytic buffer generator includes a flow-through central buffer-generating channel having an inlet and an outlet; a second chamber including a first electrode; a third chamber including a second electrode; a first ion exchange barrier configured to pass cations or anions, but not both, and to block bulk liquid flow, disposed between the second chamber and the buffer-generating channel; a second ion exchange barrier configured to pass cations or anions, but not both, and to block bulk liquid flow, disposed between the third chamber and the buffer-generating channel; a first current source connected to the first and second electrodes, wherein the generator is fluidically coupled to a chromatography apparatus; and an aqueous liquid source fluidically connected to at least one of the flow-through central buffer-generating channel, the second chamber, or the third chamber. The first ion exchange barrier may include an anion exchange barrier and the second ion exchange barrier may include a cation exchange barrier. The generator may be coupled to the chromatography apparatus upstream of a chromatography column. The generator may also be coupled to the chromatography apparatus upstream of a sample injector valve. The buffer-generating channel outlet can be fluidically coupled to the chromatography apparatus.

The generator may further include an aqueous cation source electrolyte solution in fluid communication with an inlet of the second chamber, and an aqueous anion source electrolyte solution in fluid communication with an inlet of the third chamber. In addition, the generator may also include an electrolyte solution in fluid communication with the buffer-generating channel inlet.

An electrodialytic method for generating a modified buffer solution including flowing an aqueous liquid stream through a modified-buffer generation flow channel under a pressure less than about 30 psi; and passing a current between first and second electrodes across the modified-buffer flow generation channel and the ion-source chamber to cause cations or anions, but not both, to be transported across a first ion exchange barrier to generate a modified buffer solution which exits from the modified-buffer generation flow channel, the ion source chamber being separated from the modified-buffer flow channel by the first ion exchange barrier including exchangeable cations or anions, but not both, and capable of blocking bulk liquid flow, the membrane having a surface area greater than about 0.5 $in^2$, the buffer solution having a concentration greater than about 10 mM. The ion-receiving chamber for ions may be separated by a second ion exchange membrane from the modified-buffer flow channel, the second ion exchange membrane including exchangeable ions of the same charge, positive or negative, as the exchangeable ions of the first ion exchange membrane, the current passing between the first electrode disposed in the ion source chamber and the second electrode disposed in the ion-receiving chamber via the modified-buffer flow generation chamber.

An electrodialytic method for generating a modified buffer solution can include flowing an aqueous liquid stream through a modified-buffer generation flow channel, wherein the modified-buffer generation flow channel is separated from a first ion-source chamber by an anion exchange membrane capable of blocking bulk liquid flow and wherein the modified-buffer generation flow channel is separated from a second ion-source chamber by a cation exchange membrane capable of blocking bulk liquid flow; and passing a current between first and second electrodes across an ion-source chamber to cause cations to be transported across a cation exchange membrane and to cause anions to be transported across an anion exchange membrane, wherein the first and second electrodes are disposed within the first and second ion source chambers, respectively, and are separated from the modified-buffer flow channel; thereby generating a modified buffer solution which exits from the modified-buffer generation flow channel.

An electrodialytic buffer generator can include a flow-through central buffer-generating channel having an inlet and an outlet; a second chamber including a first electrode; a third chamber including a second electrode outlet; an ion exchange barrier, capable of passing cations but not anions and of blocking bulk liquid flow, disposed between the first chamber and the buffer-generating channel; a bipolar membrane, configured to split water and generate hydronium ions and hydroxide ions, and also to block bulk liquid flow, disposed between the third chamber and the buffer-generating channel; a first current source connected to the first and second electrodes, wherein the generator is fluidically coupled to a chromatography apparatus; and an aqueous ion source fluidically connected to at least one of the flow-through central buffer-generating channel, the second chamber, or the third chamber.

BRIEF DESCRIPTION OF THE DRAWINGS

FIG. 1 is a schematic of an exemplary device.

FIG. 14 is Table 1, which tabulates the conductance data of FIG. 7.

FIG. 15 is Table 2, which tabulates the pH data of FIG. 7.

FIG. 16 is Table 3, which tabulates the conductance data of FIG. 13.

FIG. 17 is Table 4, which tabulated the pH data of FIG. 13.

DETAILED DESCRIPTION OF PREFERRED EMBODIMENTS

Figure 2B:
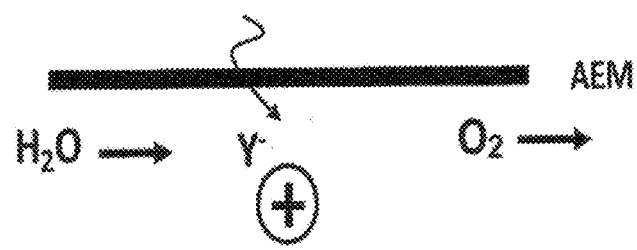
FIG. 2 is a schematic of an exemplary modified-buffer generator.

The following provides a description of buffer generators based upon electrodialytic principles and methods of using these buffer generators. In exemplary embodiments, the following provides devices and methods to generate buffers that encompass acidic to basic regime thereby allowing better control of the separation when pursuing analysis by HPLC.

In an exemplary embodiment, an electrodialytic buffer generator includes:

(a) a flow-through central modified buffer-generating channel having an inlet and an outlet;

(b) a second channel including a first electrode, the channel having an inlet and an outlet;

(c) a third channel including a second electrode, the channel having an inlet and an outlet;

(d) a cation exchange barrier, capable of passing cations but not anions and of blocking bulk liquid flow, disposed between the first channel and the buffer-generating channel;

(e) an anion exchange barrier, capable of passing anions but not cations and of blocking bulk liquid flow, disposed between the third channel and the buffer-generating channel; and a first current source connected to the first and second electrodes.

In an exemplary embodiment, the device is installed in the low pressure side of the chromatograph. FIG. 1 shows an exemplary schematic of this embodiment. The reservoir 10 contains the source electrolyte or DI water source 12 and is connected to the input of the proportioning valve 22 via conduit 14. An optional reservoir 16 contains either DI water or the solvent is also connected to the input of the proportioning valve 22 via conduit 20. Usually three to four reservoirs can be connected to the proportioning valve. An optional degasser 26 and 28 may be used to degas the respective streams in lines 14 and 20. The proportioning valve output is connected to the pump 30. This placement is called a low pressure installation as the pH generator module 24 is placed between the reservoir and the proportioning valve or between the proportioning valve and the input side of the pump 30 at the location 24*b*. The output of the pump is routed as in a standard HPLC system to an injection valve. The above placement allows automated generation of the buffer using the low pressure pH generators described herein. In this configuration due to the placement ahead of the pump input mandates that the device back pressure is low to facilitate operation without cavitation. This constraint is not present with devices operated on the high pressure side of the pump. The reservoirs described herein may be pressurized as shown by gas stream 34 and 36 which comprises of nitrogen or helium. In operation the device of the present invention will generate the buffer in an (diluted if needed) electrolyte stream which may be mixed with a suitable solvent and then fed to the input side of a pump. This configuration permits the separation to be conducted at high pressures using a low pressure pH generator module.

Several configurations are feasible in implementing the embodiments described herein. In one configuration a commercial suppressor is used to generate buffers on the low pressure side of the pump.

In an exemplary embodiment, the first and third channels are ion-receiving flow channels. Ion-receiving flow channels are separated from the modified buffer-generating channel by an ion exchange barrier, which prevents bulk liquid flow across the barrier. The ion-exchange barrier is optionally a cation exchange barrier, an anion exchange barrier, or a bipolar ion exchange barrier. An exemplary bipolar ion exchange barrier has the properties of both an anion exchange barrier and a cation exchange barrier. In various embodiments, the barrier is a membrane.

Figure 3A:
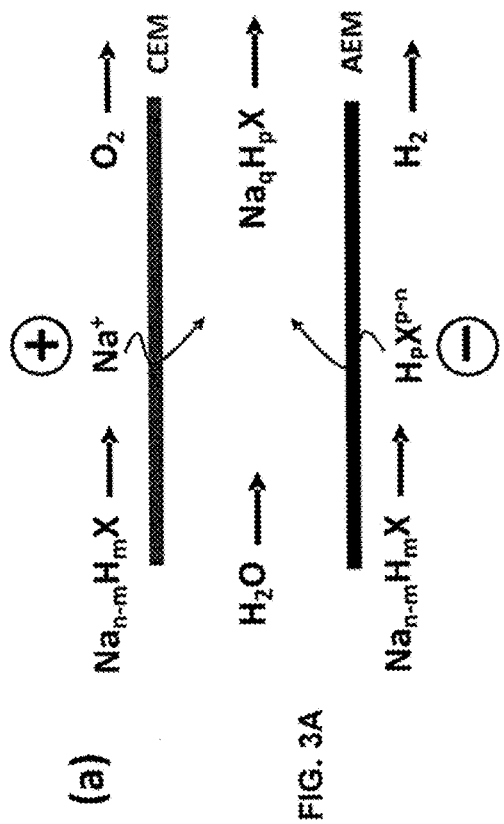
FIG. 3 is a schematic of an exemplary modified-buffer generator.
Figure 3B:
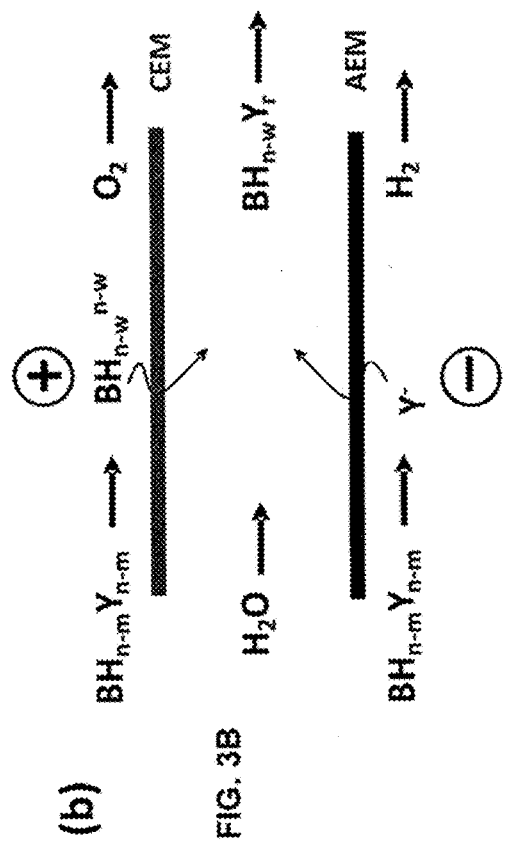
Figure 4:
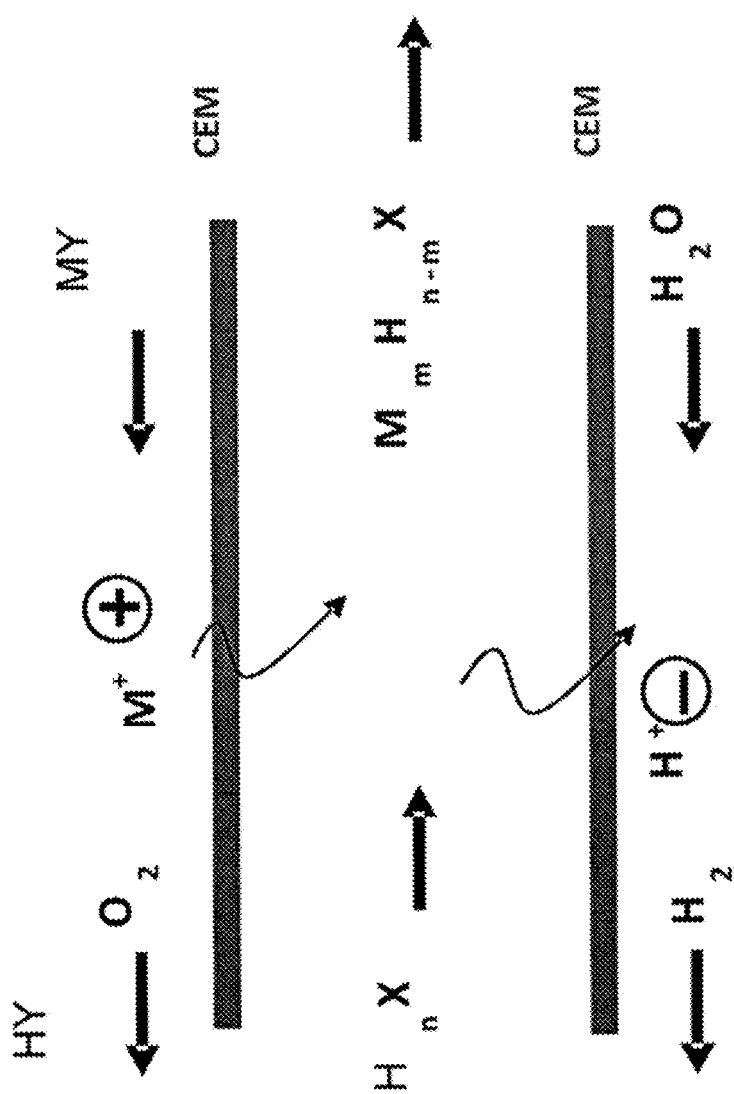
FIG. 4 is a schematic of an exemplary modified-buffer generator.

In another embodiment, electrodialysis devices are shown in FIG. 2, FIG. 3 and FIG. 4. In this design the device comprises a central channel that is bounded by an anion exchange and cation exchange membrane. By installing two electrodes in the vicinity of the membrane, e.g., within two regenerant channels (e.g., ion-receiving flow channel) as per the embodiments herein, buffers can be generated. For example when the polarity is in the deionizing mode as illustrated in FIG. 2(*a*), the ions are removed from the central buffer generating channel and the applied current dictates the amount removed. This design is simpler to implement and requires only one power supply. This mode of operation is called the "Removal mode". The current can be varied in an increasing or decreasing fashion to generate the desired pH gradient of interest provided the appropriate buffer ions are present.

Referring to FIGS. 2(*a*) and 2(*b*), the transport of the cations from the central buffer generating channel towards the cathode via the cation exchange membrane, along with transport of anions from the central channel towards the anode via the anion exchange membrane allows modification of the electrolyte to a buffer that can be programmed in pH and ionic strength.

The central channel from the above design in another embodiment is fed with the electrolyte that to be modified, e.g., ethylenediamine/tripotassium citrate (50 mM/50 mM) and is pumped at a selected flow rate, e.g., 0.5 ml/min. In an exemplary embodiment 0.2 M potassium nitrate solution is fed as the regenerant at a selected flow rate, e.g., 2.5 ml/min. Upon application of a current gradient a pH gradient is readily established using this setup.

If the above device is operated in a reversed polarity to the deionizer mode then ions can be introduced to the central buffer generating channel. These ions can be electrolysis ions or electrolyte supplied ions or the combination of the two. FIG. 3 shows the schematic of this design. This is the "Addition Mode", which is simple to implement and requires only one power supply.

Referring to FIG. 3(*a*) and FIG. 3(*b*), sodium can be added into the central channel along with addition of an anion resulting in a buffer generation. Note that B represents a cation that can migrate across the cation exchange membrane such as, for example, $H^+$, $Na^+$, or $K^+$. In addition, Y represents an anionic species that can migrate across the anion exchange membrane such as, for example, $OH^-$, $PO_4^{3-}$, $HPO_4^{2-}$, or $H_2PO_4^{1-}$. X represents an anionic species and $Na_2HPO_4$ represents an example of a strong base salt. It should be noted that the contents of the regenerant channel can be altered and thus selectively adding other species of interest via the ion exchange membrane. In the above example if the anode channel is fed with sodium containing electrolyte the sodium is transported to the central channel proportional to the current applied. If water is transported then $H^+$ is transported to the central channel thereby altering the pH of the product. Thus many possibilities for buffer generation exist.

It is also possible to use a device that is a combination of the "Addition mode" and/or "Removal mode" by reversing the polarity of the electrode(s). Thus, this device provides a buffer generation system to add or remove ions as needed. Similarly it is also possible to switch the polarity to use the same device to switch from the "Addition mode" to the "Removal mode" of operation in a programmed fashion. It is a feature of the instant invention that additional channels can be added to the present configuration as needed.

In another mode of operation in place of the salt stream the device of the present invention modifies an acid or base stream and generates the desired buffer. This is illustrated in FIG. 4. Referring to FIG. 4, the acid such as boric acid ($H_nX$) is pumped into the buffer generator channel, the exterior channels are swept with a base (e.g., NaOH and represented as MY) where the cation component of the base would be injected into the central buffer generator channel from the anode via the cation exchange membrane and used to adjust the pH of the buffer. An equivalent number of hydronium ions would be driven to the cathode via the cation exchange membrane close to the cathode and will combine at the cathode to form DI water. Thus by varying the current a gradient can be established in the product stream.

In various embodiments the generator of the invention further comprises:

(f) an aqueous cation source electrolyte solution in fluid communication with the second channel inlet, and (g) an aqueous anion source electrolyte solution in fluid communication with the third channel.

In various embodiments, the generator of the invention further comprises:

(f) an electrolyte solution in fluid communication with the buffer-generating channel inlet.

Figure 23:
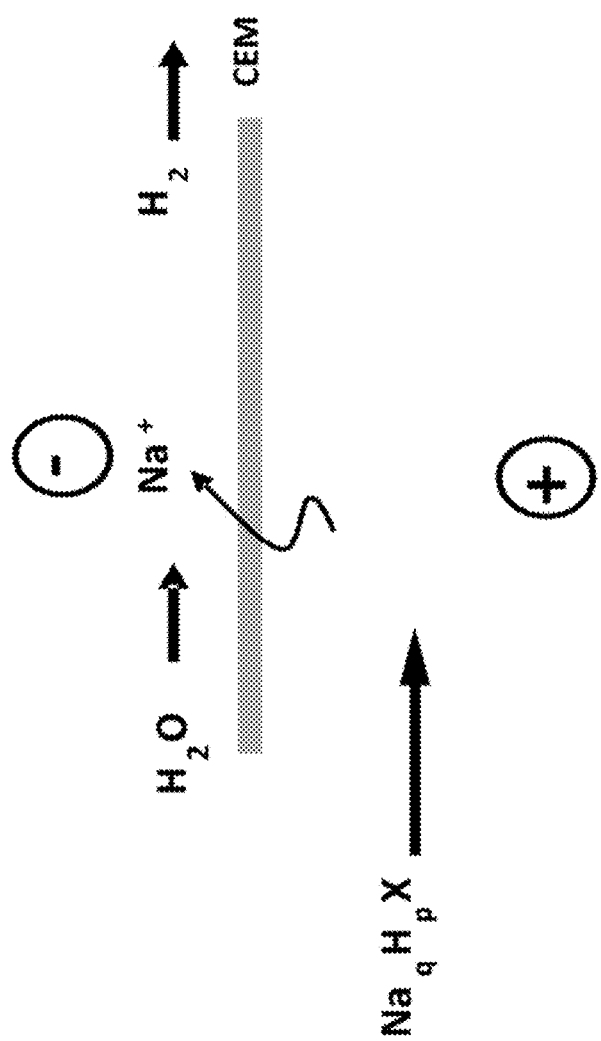
FIG. 23 is a schematic of an exemplary modified-buffer generator that uses only one ion exchange barrier.

FIG. 23 illustrates a schematic of a modified-buffer generator that uses only one ion exchange barrier. This device includes a modified buffer generating channel including an inlet and an outlet; and an ion channel also including an inlet and an outlet. As illustrated in FIG. 23, the device includes a cation exchange barrier, capable of passing cations, but not anions and of blocking liquid flow. The cation exchange barrier is disposed between the modified buffer generating channel and the ion channel. A first current source can be electrically connected to a first and second electrodes where the first electrode is in fluidic contact with the modified-buffer generator and the second electrode is in fluidic contact with the ion channel. As illustrated in FIG. 23, the first electrode is a cathode and the second electrode is an anode. Similar to the device in FIG. 2(a), cations are removed from the modified buffer generating channel and the applied current dictates the amount removed. The anode can split water to form hydronium ions in the modified buffer generating channel to modify the pH. In alternative embodiments to the modified-buffer generator of FIG. 23, the current can be applied such that the first electrode is an anode and the second electrode is a cathode. In another alternative embodiment, the cation exchange barrier may be switched with an anion exchange barrier. In yet another alternative embodiment, the ion channel may be replaced with a chamber where the solution in the chamber is static and substantially non-flowing.

The buffer generator of the invention can be used to generate buffers for chromatographic applications, e.g., separations, e.g., ion chromatography. In various embodiments, the buffer generator is coupled to one or more components of a chromatographic separation device. In an exemplary embodiment, the buffer generator is fluidically coupled to a chromatography column. In an exemplary configuration, the buffer generator is fluidically coupled at the head of a chromatography column above (i.e., upstream) the injector valve. In various embodiments, the outlet of the flow-through central modified buffer-generating channel is fluidically coupled to the head of the chromatography column. In an exemplary embodiment, this outlet is fluidically coupled above (i.e., upstream) the sample injection valve.

Also provided by the instant invention are methods of generating buffers using the generator of the invention. Thus, in an exemplary embodiment, the invention provides a method an electrodialytic method for generating a modified buffer solution. The method includes:

(a) flowing a buffer solution, including cations and anions, at a concentration greater than about 10 mM through a modified-buffer generation flow channel under a pressure less than about 30 psi, said modified-buffer generation flow channel including a first electrode disposed therein;

(b) flowing an aqueous liquid stream through a first ion-receiving flow channel including a second electrode disposed therein. The ion-receiving flow channel is separated from the modified-buffer generation flow channel by an ion exchange barrier including exchangeable cations or anions, but not both. The barrier is capable of blocking bulk liquid flow. In an exemplary embodiment, the membrane has a surface area greater than about 0.5 in$^2$.

The method of the invention further includes, (c) passing a current between the first and second electrodes across the modified-buffer flow generation channel and the ion-receiving flow channel to cause the cations or anions, but not both, to be transported from the modified-buffer flow channel across the first ion exchange barrier into the ion-receiving flow channel to generate a modified buffer solution which exits from the modified-buffer generation flow channel.

In various embodiments, the method of the invention further comprises: (d) flowing an aqueous liquid stream through a source channel for hydrogen ions or hydroxide ions separated by a second ion exchange membrane from said modified-buffer flow channel, said second ion exchange membrane including exchangeable ions of the same charge, positive or negative, as the exchangeable ions of said first ion exchange membrane.

In various embodiments, the current is between two electrodes, each in one of two ion-receiving flow channels, each of which are separated from the modified-buffer flow channel by an ion-exchange barrier.

In an exemplary embodiment, the invention provides an electrodialytic method for generating a modified buffer solution. An exemplary method includes:

(a) flowing a buffer solution, including cations and anions through a modified-buffer generation flow channel. The modified-buffer generation flow channel is separated from a first ion-receiving flow channel by an anion exchange membrane capable of blocking bulk liquid flow. The modified-buffer generation flow channel is separated from a second ion-receiving flow channel by a cation exchange membrane capable of blocking bulk liquid flow;

(b) flowing an aqueous liquid stream through the first and second ion-receiving flow channels separated from the modified-buffer flow channel; and (c) passing a current between first and second electrodes across the modified-buffer flow generation channel and at least one ion-receiving flow channel to cause cations or anions to be transported across a member selected from the anion exchange membrane and the cation exchange membrane into a member selected from the first ion-receiving flow channel and the second ion-receiving flow channel, respectively, thereby generating a modified buffer solution which exits from the modified-buffer generation flow channel. In an exemplary embodiment, the first and second electrodes are disposed within the first and second ion receiving flow channel, respectively. In an exemplary embodiment, the first and second electrodes are disposed within the first or second ion receiving flow channel and the modified-buffer generation channel, respectively.

In various embodiments, the invention provides a method as set forth above in which a member selected from cations and anions is transported from the modified-buffer channel into a member selected from the ion-receiving flow channel and the source channel.

In an exemplary embodiment, there is provided a method of generating a buffer as set forth above in which the modified buffer solution has a concentration of ions proportional to the current through a member selected from said first electrode and said second electrode.

In various embodiments, there is provided a method of generating a buffer as set forth above in which a member selected from cations and anions flows from the ion-receiving channel.

In various embodiments, the method of the invention further comprises utilizing the buffer generated in a separation process, e.g., chromatography. Thus, in an exemplary embodiment, the method of the invention further includes, following generation of the buffer, injecting a sample with analyte ions to be separated into the modified buffer exiting the generator and separating the analytes. In an exemplary embodiment, the buffer solution flowing to the modified-buffer flow channel has not been previously generated by an electrolytic eluent generator.

In an exemplary embodiment of the device and/or methods of the invention, a bipolar membrane is used. A bipolar membrane is a layered membrane including of a cationic side that is permeable to cations and an anionic side permeable to anions. On the whole the bipolar membrane will not transportionic species from one side of the membrane to the other side. The bipolar membrane splits water molecules and produces hydronium and hydroxide ions in an applied electric field. In operation, the anion exchange membrane has to face the anode while the cation exchange membrane has to face the cathode. Thus the bipolar membrane is a convenient means of forming hydronium and hydroxide ions without the formation of gas.

Unlike electrode reactions, the bipolar membrane water splitting reaction does not follow faraday's law and the applied current has a loose relationship with the generated concentration of ions. This implies the bipolar membrane based devices require a calibration at a given current in order to determine the concentration. This also implies that the bipolar membrane based devices are current inefficient. Nevertheless these membranes could be used as per the present invention to transport hydronium and hydroxide ions thereby manipulating the buffer concentration and pH.

Figure 18:
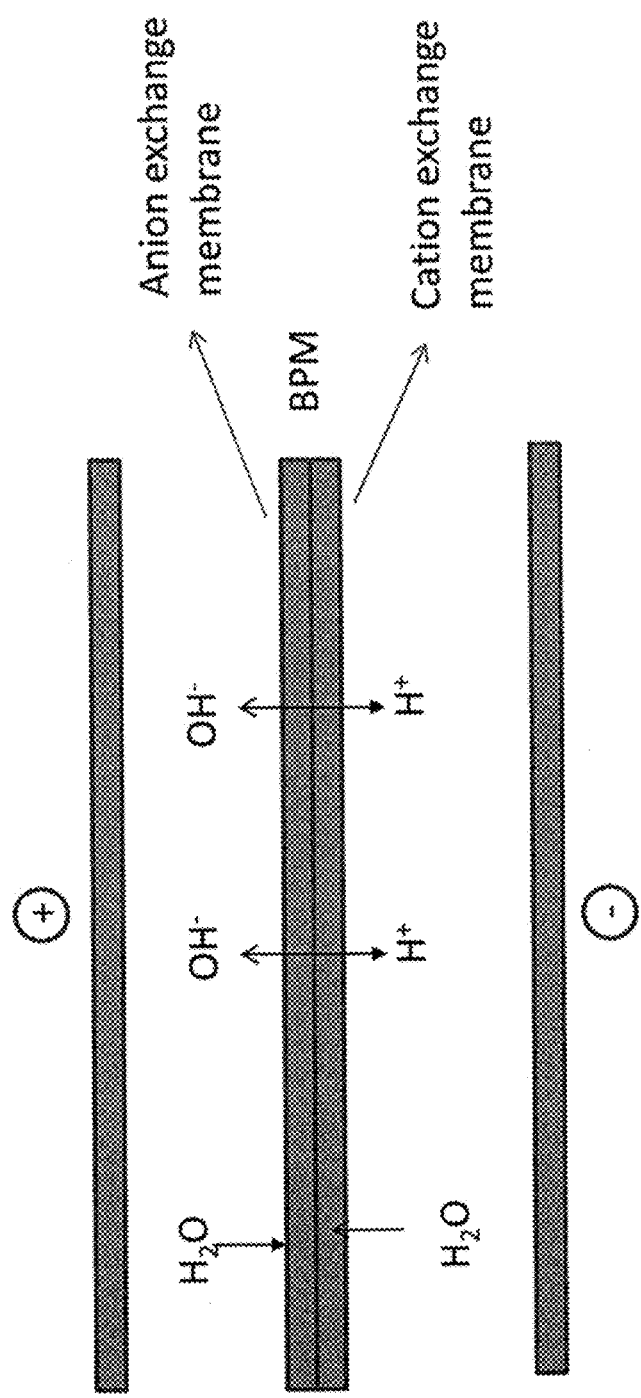
FIG. 18 is a general schematic of a bipolar membrane in an electric field.
Figure 19:
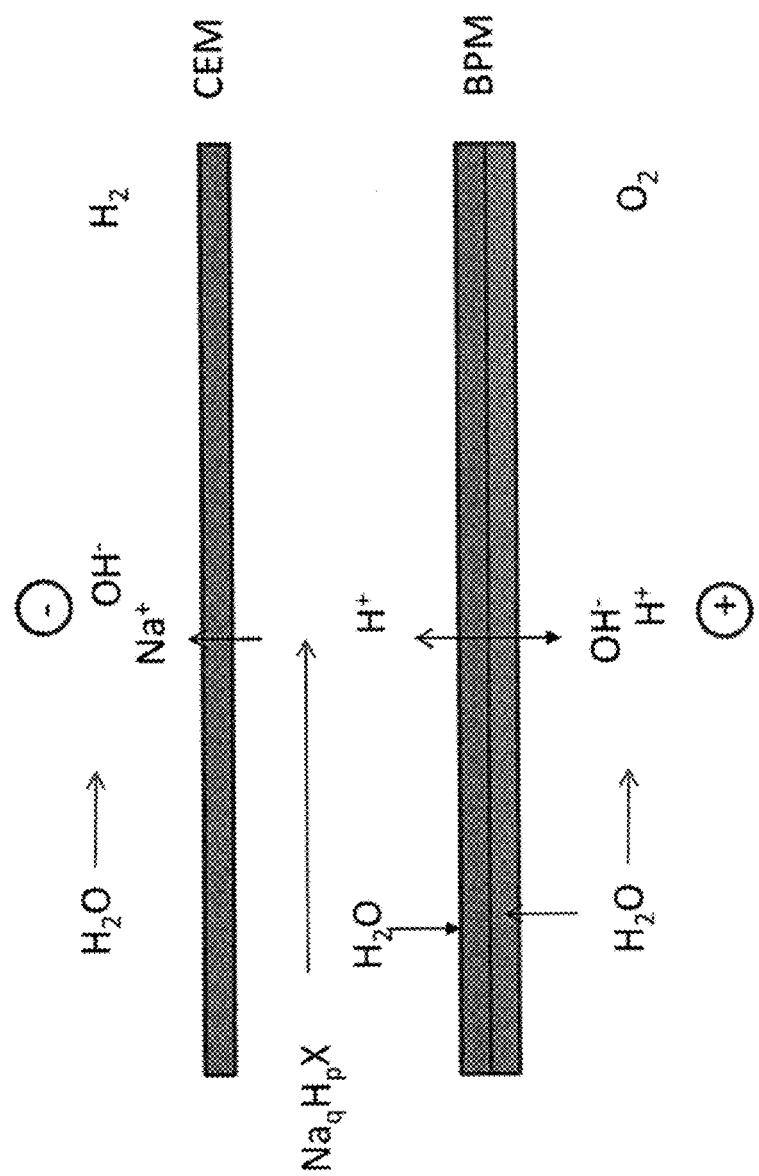
FIG. 19 is a buffer device where a bipolar membrane is used in conjunction with a cation exchange membrane to define a central eluent channel.

FIG. 18 is a general schematic of a bipolar membrane in an electric field. FIG. 19 is a buffer device of the present invention where a bipolar membrane is used in conjunction with a cation exchange membrane to define a central eluent channel. In this setup the function of the bipolar membrane is to supply hydronium ions while the cation exchange membrane removes cationic species from the buffer stream. The orientation of the bipolar membrane is arranged to provide hydronium ions in the central eluent channel. In the simplest case a salt solution supplied to the eluent channel would be converted to an acid stream by the exchange of the cation for hydronium ions in this setup. Thus this setup provides a convenient means of adjusting the pH of the influent solution without any added gas in the product. Another example would be converting a base stream to water which is a convenient means of adjusting the concentration. An applied current would generate a fixed concentration of hydronium ions which could be easily monitored by monitoring the pH of the effluent. The electrode chambers in the above example have platinum electrodes and are fed with aqueous streams to provide the water required for the water splitting reactions on the electrode. Upon applying a potential the electrodes form hydronium and hydroxide on the anode and the cathode respectively. Electrolytic gases hydrogen and oxygen are generated from the water splitting reaction on the cathode and anode respectively and are swept out of the regenerant channel. The hydroxide ions generated on the bipolar membrane combines with the hydronium ions generated on the anode electrode to form water. The cations removed by the cation exchange membrane are driven to the cathode and combine with the hydroxide to form a base. The cations in the eluent stream are exchanged for hydronium and a modified stream exits the eluent channel.

Figure 20:
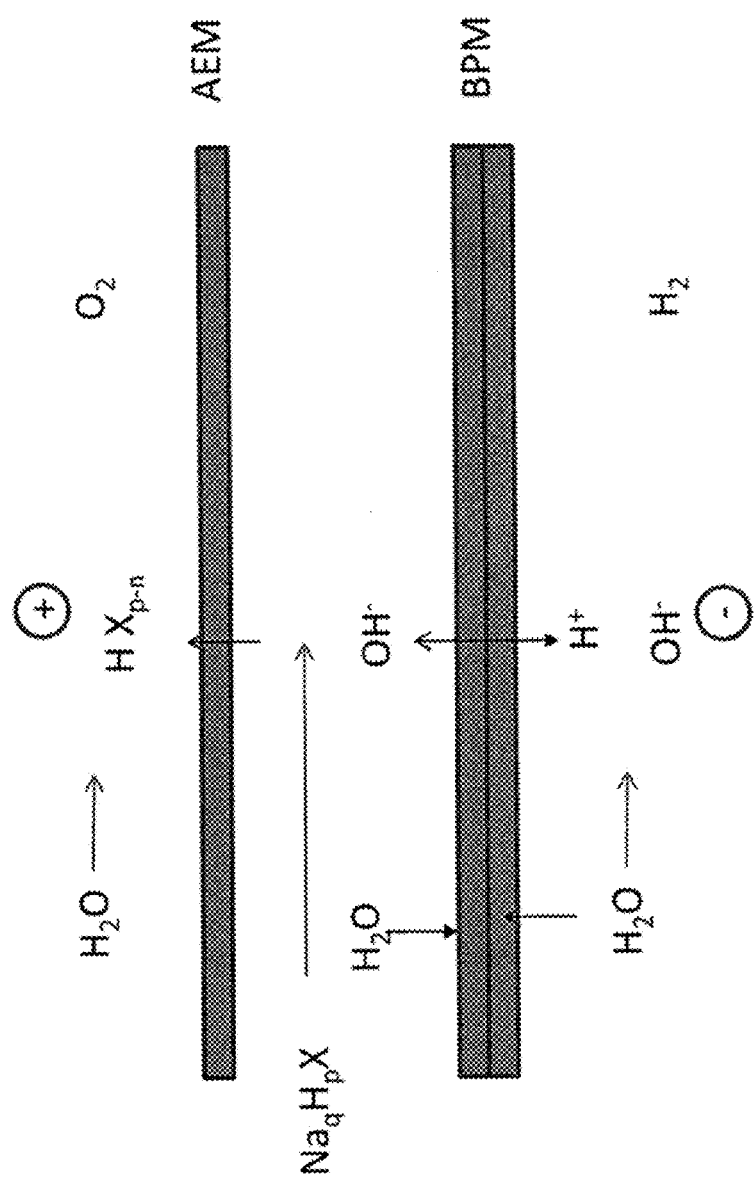
FIG. 20 is similar to FIG. 19 except the cation exchange membrane was replaced with an anion exchange membrane and the polarity was reversed.

FIG. 20 is similar to FIG. 19 except the cation exchange membrane was replaced with an anion exchange membrane and the polarity was reversed. The net effect is that the device now can conveniently add hydroxide ions and replace the anions in the eluent stream with hydroxide. In the simplest case an acid would be converted to water thus controlling the concentration or a salt solution would be converted to a base thus modifying the pH of the eluent stream. In operation the hydronium generated by the bipolar membrane combines with the hydroxide generated by the cathode to form water. The hydroxide generated by the bipolar membrane replaces the anions that are transported across the anion exchange membrane while the hydronium generated by the bipolar membrane combines with hydroxide generated on the cathode. The anions removed by the anion exchange membrane combines with hydronium ions generated by the anode. The overall modification of the incoming buffer is feasible by this removal approach.

Figure 21:
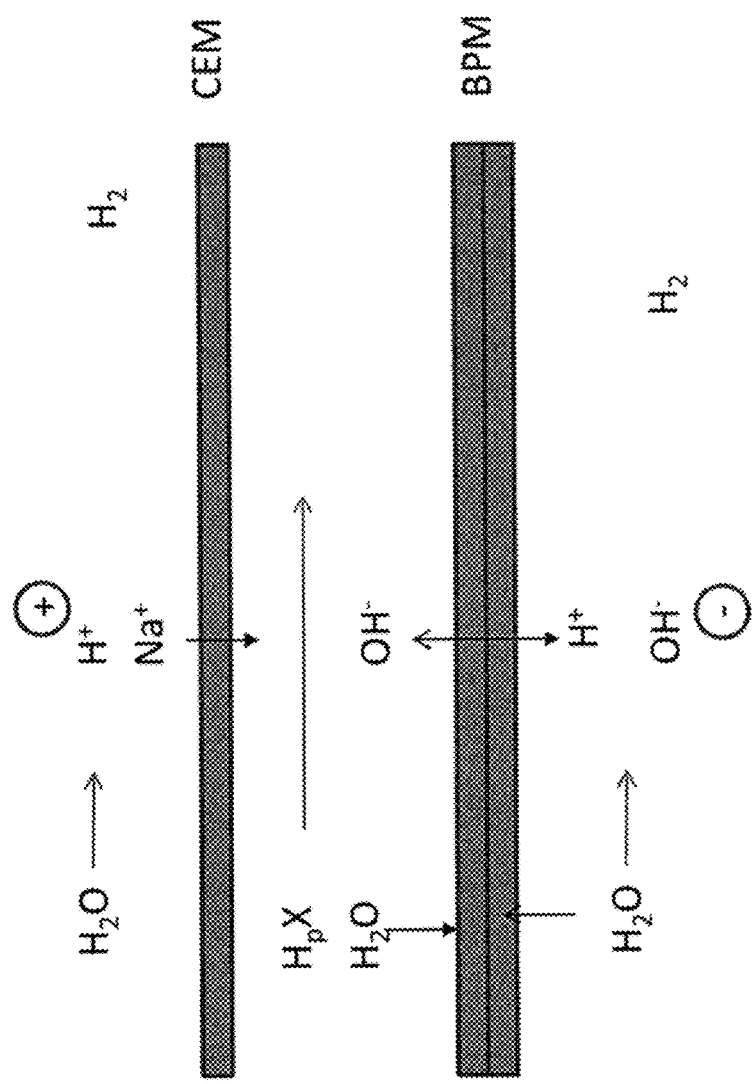
FIG. 21 shows a setup where a cation exchange membrane is used to supply a cationic component of a reagent supplied to the anode regenerant channel.
Figure 22:
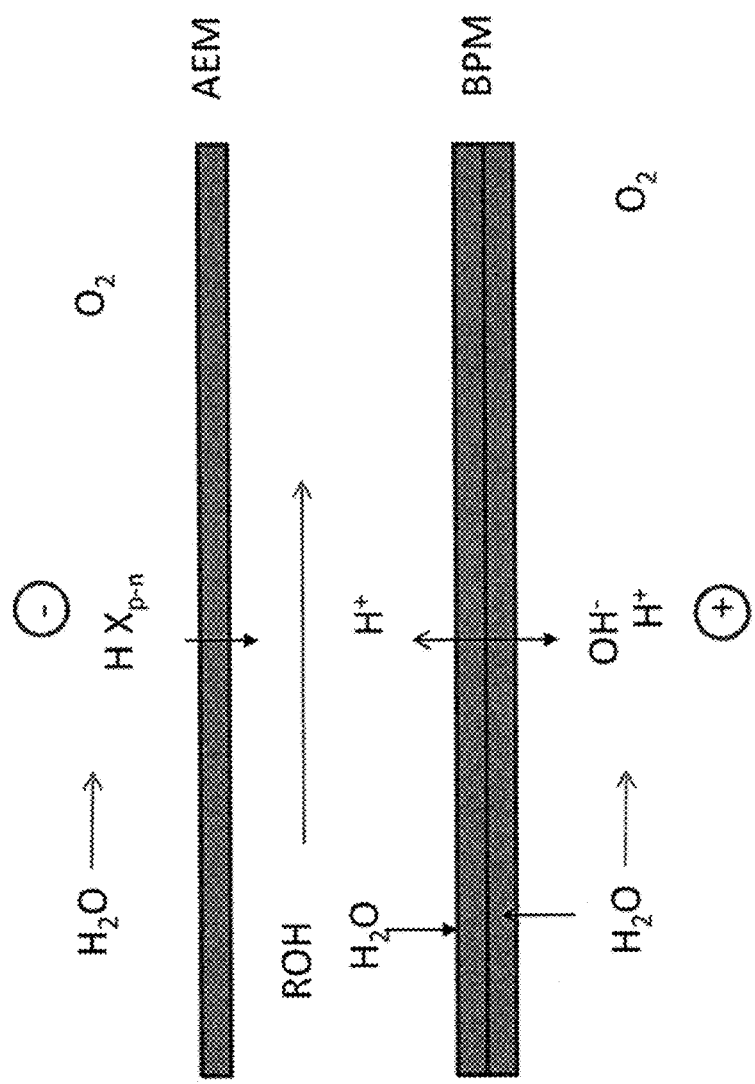
FIG. 22 shows a setup for acid addition.

FIG. 21 and FIG. 22 are additive approaches where the anion or cation component of a reagent could be added as an acid or base using a device containing a bipolar membrane. FIG. 21 shows a setup where a cation exchange membrane is used to supply a cationic component of a reagent supplied to the anode regenerant channel. For example if sodium hydroxide is supplied to this channel then sodium would be transported by the applied field and will enter the eluent channel. At the same time a hydroxide ion generated by the bipolar membrane will also enter the eluent channel to maintain electroneutrality. Thus a base addition is feasible into the eluent channel. FIG. 22 shows a setup for acid addition.

In summary the use of the bipolar membrane provides a convenient means of adding hydronium or hydroxide into the eluent channel while adding or removing selected components anions or cations from the buffer generating channel without the presence of gases.

The following examples are offered to illustrate, not to limit, the scope of the invention.

EXAMPLES

Example 1

1a. Principles

Figure 5:
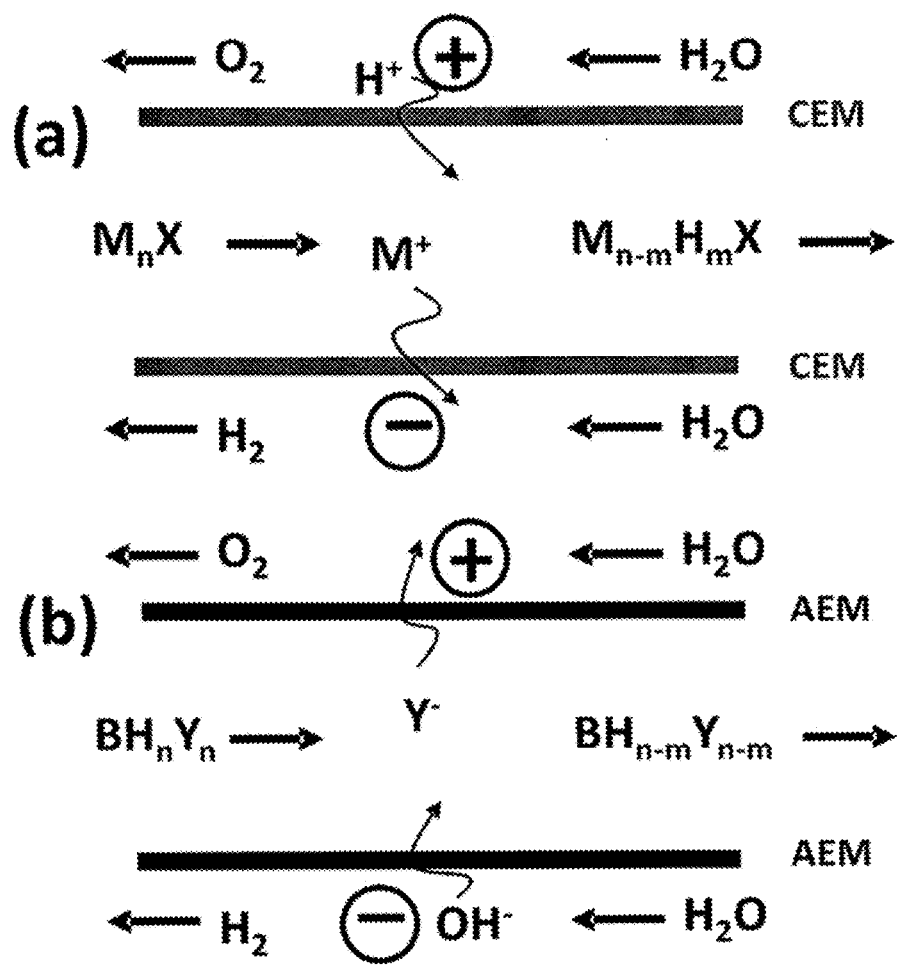
FIG. 5 is a EBG scheme with (a) an anion suppressor (a dual CEM device) with the strong base salt of a multiprotic acid as the feed solution and (b) a cation suppressor (a dual AEM device) with the strong acid salt of a multiprotic base as the feed solution. The drive current controls how much of the strong base cations in (a) and the strong acid anions in (b) are respectively removed of the system thus attaining the desired pH.

Suppressor-based Electrodialytic Buffer Generators. A solution of the fully neutralized Na salt of a n-protic acid, $Na_nX$, is influent into a CEM-based suppressor, as illustrated in FIG. 5(a) and the $Na^+$ is at least partially electrodialytically removed by current I and replaced. For simplicity, a NaX-HX buffer system was assumed but the general scheme is applicable to corresponding multiprotic acid-base systems. NaX flows through the central channel at Q mL/min and at a molar concentration C while a current i mA is made to flow through the system. Under conditions when significant concentration of non-$H^+$/non-$OH^-$ ions remain to be transported, the efficiency of present suppressors can be taken to be Faradaic. At steady state, 0.06 i/F moles/min of $Na^+$ is removed to the negative electrode compartment from the center and an equal amount of $H^+$ from the anode compartment is introduced. This amounts to HX formation in the center channel equal to 60i/FQ M, while NaX concentration drops to C-60 i/FQ M. Neglecting activity corrections for the moment, the pH is then simply computed from the familiar Henderson-Hasselbalch equation as:

$$pH = pK_a + \log(CFQ - 60\ i)/60\ i \qquad (1)$$

This is usable in the range when an appreciable amount (e.g. >5%) of HX has formed but also an appreciable amount of NaX remains (and $[Na^+]$ still remains >>$[H^+]$). At low pH if $[H^+]$ in the central channel becomes comparable to $[Na^+]$, we can no longer assume that $Na^+$ transport is the sole Faradaic process. Also, at high HX values, HX can be lost through the ion exchange membranes as there are no barriers towards the transport of neutrals. However, there is no influence of the electric field on the electrical transport of a neutral species and the loss through the membrane, driven by the concentration difference, in most cases is not large. Such losses can also be avoided by using a buffer system based on a multiprotic acid/base. For example if a molar concentration C of $Na_3PO_4$ or $Na_3Citrate$ is introduced into the system, current controlled $H^+$—$Na^+$ exchange can create an adjustable pH buffer system. There will be no loss of the neutral acid until significant amounts of the free acid forms at the high end of the exchange. For the general case of the introduction of the solution of a fully neutralized salt $(M_nX)$ of a n-protic acid $(H_nX)$ being introduced into the system, the charge balance equation is:

$$\left(nC - \frac{60i}{FQ}\right) + [H^+] - \frac{K_W}{[H^+]} - pC\sum_{p=1}^{n}\alpha_p = 0 \quad (2)$$

where the first term indicates the remaining M$^+$ concentration and $\alpha_p$ indicates the fraction of the total anion that exists with a charge of p−. The general procedure for solution, including activity corrections, is given in Example 1c.

An electrolytic buffer generator (EBG) based on a weak base and its salt proceeds very much the same way. The general case is that of a base which can take up to n protons and a solution of the fully neutralized salt BH$_n$Y$_n$ is influent into an AEM-based suppressor. Some (or all) of the Y$^-$ is removed to through the AEM to the anode compartment while an equal amount of OH$^-$ enters from the cathode compartment to neutralize H$^+$ (FIG. 1b). For the simple case of a monoacidic base B and its salt BHY, eq 1 still applies with K$_a$ being the acid dissociation constant of BH$^+$ and the sign of the log-term reversed:

$$pH = pK_a - \log(CFQ - 60\ i)/60\ i \quad (3)$$

The use of a multiprotic base will avoid loss of the free base and the applicable equation will be similar to eq 2.

A suppressor based EBG has the advantage that the device is commercially available and many commercial ICs allow current programming of the suppressor. In principle, no gas is evolved in the fluid channel of interest. The buffer concentration is fixed; a constant buffer ion concentration is maintained while pH is adjusted by applying controlled removal of the counterion. The approach can thus be thought of as subtractive. While the counterion is subtracted, H$^+$ or OH$^-$ (as appropriate) takes its place to maintain charge balance. It is interesting to note that the system is not operationally symmetric: It is possible to introduce Na$_2$HPO$_4$ and render it into NaH$_2$PO$_4$ quite effectively and efficiently by removing Na$^+$, but it is not possible to predictably and efficiently convert NaH$_2$PO$_4$ into Na$_2$HPO$_4$ by current controlled Na$^+$ introduction from the anode compartment; this will result in an equal amount of sodium being lost to the cathode compartment. This does not mean, however, that a temporally increasing pH gradient will not be possible with a CEM-suppressor based EBG with a phosphate buffer. Such a system will use a temporally negative current gradient.

Example 1b

Experimental Section

Reagents. All chemicals were commonly available reagent grade and distilled deionized water was used throughout. See Example 1c.

Disodium hydrogen phosphate heptahydrate and sodium citrate dihydrate was purchased from Mallinckrodt. Ethylenediamine dihydrochloride was purchased from Acros Organics. Tris(hydroxymethyl)aminomethane hydrochloride and dipotassium hydrogen phosphate was purchased from J. T. Baker. All the chemicals are reagent grade and solutions were prepared with 18.2 MΩ·cm Milli-Q (Millipore) deionized water.

Figure 12:
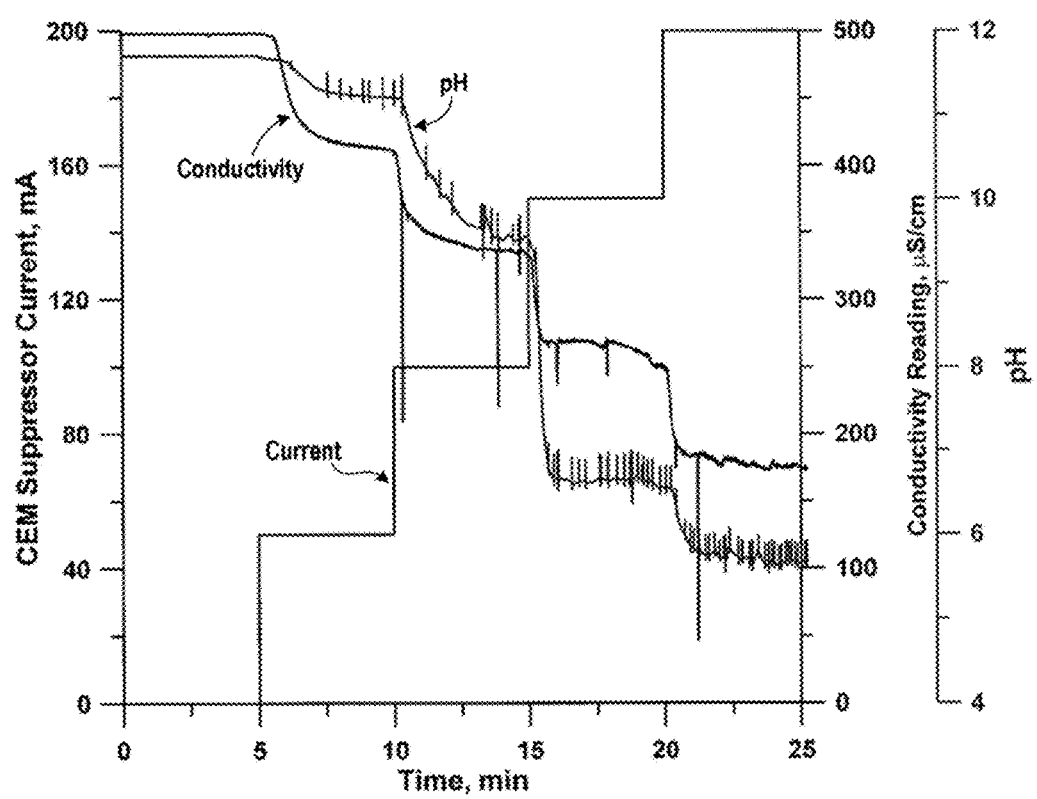
FIG. 12 is a noise observed in absence of the CRD gas removing device. The pH electrode flow cell has essentially no back pressure and the pH trace shows increasing noise spikes with increasing current. Noise is also observed on the conductivity trace with greater frequency at increased current levels (aside from spikes, look at the thicker trace that is the result of noise from micro bubbles). The current program is shown a line having a staircase pattern (left ordinate).
Figure 13:
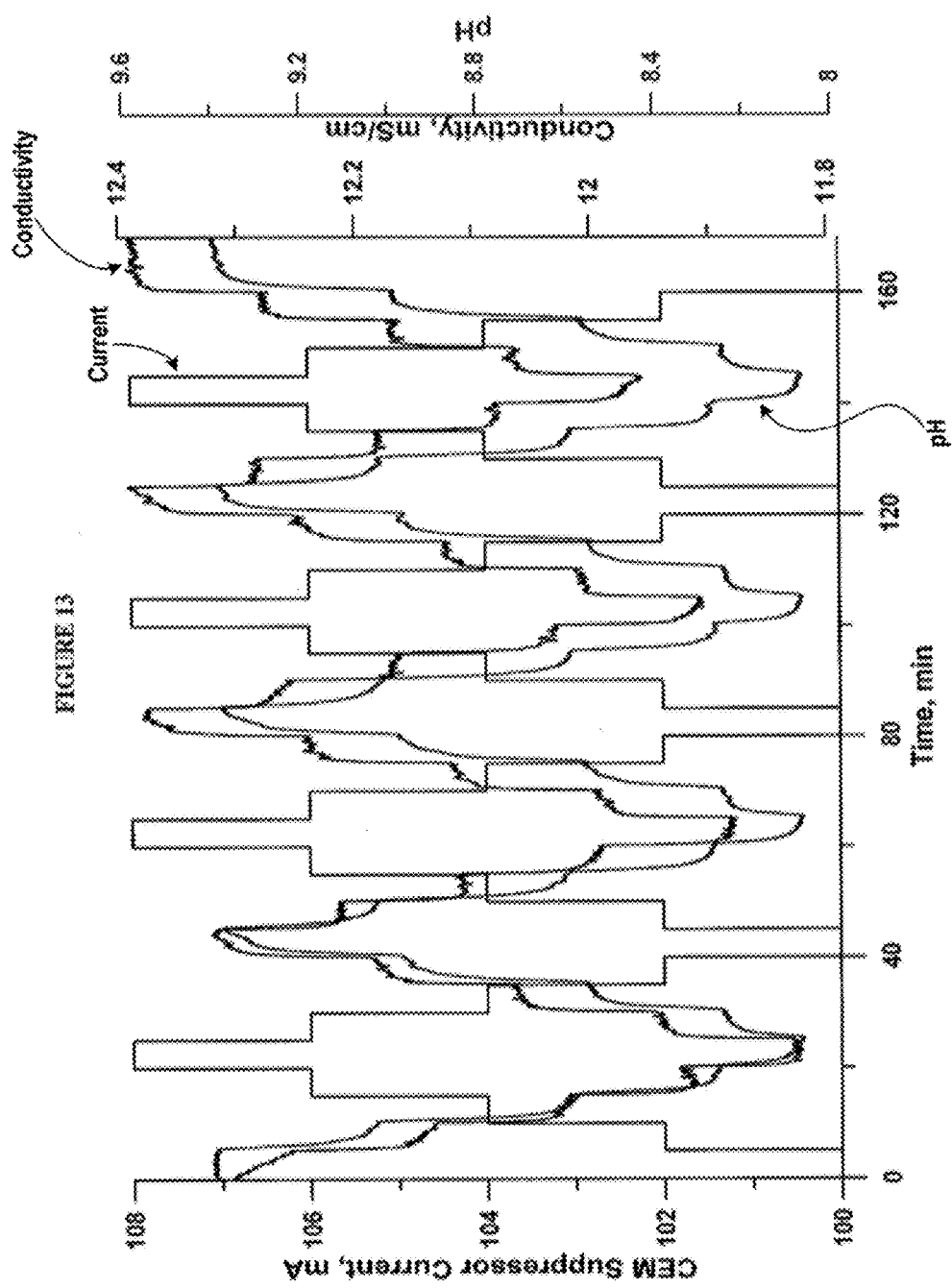
FIG. 13. Repeatability and reproducibility of small current steps. Detailed numerical data are presented in Tables 3 and 4.

Noise was observed in absence of the CRD gas removing device, as illustrated in FIG. 12. The pH electrode flow cell has essentially no back pressure and the pH trace shows increasing noise spikes with increasing current. Noise is also observed on the conductivity trace with greater frequency at increased current levels (aside from spikes, look at the thicker trace that is the result of noise from micro bubbles). The current program is shown as a line having a staircase shape (left ordinate).

This Excel™ based calculation is demonstrated using the system of FIG. 5a; this is also attached as separate file as Mater pH.xlsx. Details regarding these calculations can be found in Anal. Chem. 2012, 84, 67-75 and the associated Supporting Information. In the top part of the spreadsheet, the respective acid dissociation constants (K for boric acid, K$_1$, K$_2$, K$_3$ for phosphoric acid and citric acid) are respectively written down and given the names KB, KPA, KPB, KPC, KCA, KCB and KCC. The total borate, phosphate and citrate concentrations (0.045, 0.015 and 0.015 M) are respectively given the names CB, CP and CC.

In column X titled I$_{used}$, we put down some ionic strength (I) of the solution (to start with, we used 0.3). Using this trial value of this ionic strength, in columns Y:AG (respectively headed GH, GOH, GBor, GP1, GP2, GP3, GC1, GC2, and GC3) we compute the activity coefficients of H$^+$, OH$^-$, B(OH)$_4^-$, H$_2$PO$_4^-$, HPO$_4^{2-}$, PO$_4^{3-}$, H$_2$Citrate$^-$, HCitrate$^-$ and Citrate$^{3-}$, respectively, from the Davies equation:

$$-\log\gamma_i = 0.51Z_i^2\left(\frac{\sqrt{I}}{1 + 0.33d_i\sqrt{I}} - 0.3I\right) \quad (S1)$$

where Z$_i$ is the charge magnitude of ion i (respectively 1, 2, 3) and d$_i$ is the ion size parameter. Based on Kielland et al. (J. Amer. Chem. Soc, 1937, 59, 1675-8), the ion size parameters of H$^+$, OH$^-$, H$_2$PO$_4^-$, HPO$_4^{2-}$, PO$_4^{3-}$, H$_2$Citrate$^-$, HCitrate$^-$ and Citrate$^{3-}$ to be 9, 3.5, 4.25, 4, 4, 3.5, 4.5 and 5; d$_{B(OH)4-}$ was estimated to be 6. Based on the these activity coefficients the equilibrium constants KW, KB, KPA, KPB, KPC, KCA, KCB and KCC were calculated in concentration terms in columns AI:AP titled respectively CKW, CKB, CKPA, CKPB, CKPC, CKCA, CKCB and CKCC from the following relationships:

$$CKW = KW/(\gamma_{H+} * \gamma_{OH-}) \quad (S2)$$

$$CKB = KB/(\gamma_{H+} * \gamma_{Bor-}) \quad (S3)$$

$$CKPA = KPA/(\gamma_{H+} * \gamma_{H2PO4-}) \quad (S4)$$

$$CKPB = KPB * \gamma_{H2PO4-}/(\gamma_{H+} * \gamma_{HPO42-}) \quad (S5)$$

$$CKPC = KPC * \gamma_{HPO42-}/(\gamma_{H+} * \gamma_{PO43-}) \quad (S6)$$

$$CKCA = KCA/(\gamma_{H+} * \gamma_{H2Cit-}) \quad (S7)$$

$$CKCB = KCB * \gamma_{H2Cit-}/(\gamma_{HCit2-}) \quad (S8)$$

$$CKCC = KPC * \gamma_{H2PO4-}/(\gamma_{H+} * \gamma_{Cit3-}) \quad (S9)$$

The potassium concentration was not explicitly measured but sufficient KOH was added to adjust the pH to 12.00; since iterative calculations (vide infra) indicated that this pH was attained (to the nearest mM) with 143 mM K$^+$ (this suggests ~30.5 mM KOH was added to the concoction), we used 0.143 M K$^+$ in our calculations. This is the starting value of [K$^+$] in the column titled CK and begins in cell E9. In E9:E152 the [K$^+$] values are decremented by 0.001 M at each step to 0 in E152. In cell F9 a trial value of pH (any value between 0 and 14) is initially entered. In cell G9 [H$^+$] is computed as 10^−pH (the entry in G9 is 10^−F9). The α-values (fraction present in a specific ionic form) are defined as (K$_0$=1):

$$\alpha_i = \frac{K_0 \ldots K_i[H^+]^{n-i}}{\sum_{i=0}^{i=n} K_0 \ldots K_i[H^+]^{n-i}} \quad (S10)$$

The denominator is designated as Q, and the values for the borate, citrate and phosphate systems are computed in the columns QB, QC and QP as:

$$QB = [H^+] + KB \quad (S11)$$

$$QC = [H^+]^3 + KCA[H^+]^2 + KCA*KCB*[H^+] + KCA*KCB*KCC \quad (S12)$$

$$QP = [H^+]^3 + KPA[H^+]^2 + KPA*KPB*[H^+] + KPA*KPB*KPC \quad (S13)$$

The individual ionic concentrations were computed in columns K:R headed B, C1, C2, C3, P1, P2, P3 and OH (respectively Borate$^-$, H$_2$Citrate$^-$, HCitrate$^{3-}$, Citrate$^{3-}$, H$_2$PO$_4^-$, HPO$_4^{2-}$, PO$_4^{3-}$ and OH$^-$) based on $$[Bor^-] = CB*\alpha_{B-} \quad (S14)$$

$$[H_2Citrate^-] = CC**\alpha_{H2Cit-} \quad (S15)$$

$$[HCitrate^{2-}] = CC**\alpha_{HCit2-} \quad (S16)$$

$$[Citrate^{3-}] = CC**\alpha_{Cit3-} \quad (S17)$$

$$[H_2PO_4^-] = CC**\alpha_{H2PO4-} \quad (S18)$$

$$[HPO_4^{2-}] = CC**\alpha_{HPO42-} \quad (S19)$$

$$[PO_4^{3-}] = CC**\alpha_{PO43-} \quad (S20)$$

$$[OH^-] = CKW/[H^+] \quad (S21)$$

Now for the charge balance equation:

$$[H^+] + [K^+] - ([Bor^-] + [H_2Citrate^-] + [H_2PO_4^-] + [OH^-] + 2([HCitrate^{2-}] + [HPO_4^{2-}]) + 3([Citrate^{3-}] + [PO_4^{3-}])) = 0 \quad (S22)$$

is simply written as an expression in column S titled Poly (for Polynomial value). The whole expression was squared to make it sign-independent and multiply by a large number (in this case $10^{10}$). The latter is done to satisfy one of Solver's quirks, that it stops optimization when it decides it his close enough. The multiplier simply accentuates the difference to keep the computations ongoing.

In Column W, the ionic strength value ($I_{calc}$) was calculated based on the definition of ionic strength:

$$I_{calc} = [H^+] + [K^+] + [Bor^-] + [OH^-] + [H_2Citrate^-] + [H_2PO_4^-] + 4([HCitrate^{2-}] + [HPO_4^{2-}]) + 9([Citrate^{3-}] + [PO_4^{3-}]) \quad (S23)$$

The entire 143 rows are now filled in by copying and pasting row 9, only the values already filled in Column E for CK remain unique. On the bottom of column S154, all the values in column S were summed. We invoke Solver and ask it to minimize S154 by varying the entire pH column (F9:F152). Solver is repeated until S154 value no longer changes. Now all the computed values for $I_{calc}$ (column W) are pasted (not formulas but values: [Alt-E]-S-V) into the $I_{used}$ column (W). The difference between the two (Delta I) is also kept a tab of (column V), when this approaches $10^4$, further iteration is not meaningful. Solver is asked to recompute the values (minimize S154 etc.) and the process is repeated (rarely more than 3 cycles) before I and pH values converge. The activity of the hydrogen ion AH (equal to GH*[H$^+$]) and the activity corrected pH (PAH) are computed in columns T and U, respectively.

A flow rate of 1 mL/min is equal to 16.667 μL/s. removing 1 mM K$^+$ is 16.667 neq/s. Multiplying by the Faraday (96485 coulombs/eq) gives us the current necessary, 1.608 mA. Column D gives sequentially cumulative mM K$^+$ removed. Column C, the current needed in mA (labeled cum curr) will just be 1.608 multiplied by the value in Column D if the Faradaic efficiency $F_e$ was unity throughout.

Correction for Nonunity $F_e$. If $F_e$ is used as defined by eq 4 in the main text and use herein a value of 15 for $R_\lambda$ (the free solution value is ~5 and is expected to be much higher in a membrane, we can calculate the value of $F_e$; this is done in column A; the value of this efficiency factor will always lie between 1 and 0, tending to the latter when [H$^+$] is large relative to the ion to be removed. We assume that $F_e$ computed for the terminal results obtained in row 9 applies to the current needed for row 10 and so on. The actual current needed in the step is thus the 1.608 mA divided by $F_e$; this is thus computed in Column B. The cumulative current in Column C is thus the immediately preceding value in the cell above plus the new increment in the cell to the immediate left.

Algorithm for Iterative Correction of a Current Program to Produce a Desired pH Profile.

The basic logic is straightforward: Create an initial current vs. time profile. Record the resulting time-current-pH data. Using the observed results as a template, construct a linear (or concave/convex) pH gradient using as many of these points (or being as close to these points as possible. If this can be given in the form of an equation, the desired pH at any given time point is readily available. For a linear gradient, a straight line may well be a linear least squares fit in the desired range whose equation is readily available and this best fit line can be taken as the eventually desired profile. In order to get to this profile, at any given time point, the desired pH is looked up and the observed data is searched for what current produces this pH and this current is then used at this time point.

As an example, in iterative correction.xlsx, the first three columns list time, current and pH. Note that the lag time between a current step and the onset of the pH change was observed to be ~0.45 min and the pH data was accordingly shifted in time. The desired pH corresponding to the best linear fit in the desired range is listed in column D and the difference (observed−desired) is listed in column E as Delta pH. In the present instance, most of these values are negative, i.e., the observed pH is less than the desired pH, suggesting less potassium removal and hence less current is needed. The local slope ΔpH/Δi is computed. The desired difference ΔpH is then divided by the slope to obtain the needed current change; this is then added to the extant current program.

Electrolytic Buffer Generators. ASRS Ultra II and CSRS Ultra (both 4-mm, www.dionex.com) were used as EBG's. Electrolyte solutions were delivered by an ICS2000 IC pump through the eluent channel; water was peristaltically pumped (Gilson Minipuls 2) through the regenerant channels. The suppressor current was software programmed (Chromeleon V.6.60). The conductivity of the generated buffer solutions are much higher than the typical solutions measured by our conductivity detectors. To keep the conductance in the measurable range, we prepared high cell constant (6400 cm$^{-1}$) flow-through detection cells (two tubular electrodes separated by a spacer tube) coupled to a Dionex CD25 conductivity detector. The pH was measured after two point calibration with standard buffers. Because of concern that applied voltage in the EBG or the preceding conductivity detector may affect in-line pH-measurement, much of the initial pH measurements were made by applying constant current steps and collecting the device effluent in discrete aliquots. Since monitoring results of a programmed current profile was not practical this way, a narrow long tube was connected between the conductivity cell and the home-built pH flow cell. Experiments established that the measured pH is the same in collected aliquots and in an in-line arrangement; pH was measured in-line henceforth. However, the volume of the tubing between the conductivity flow cell and the pH electrode flow cell, the significant volume of the latter, the slower response of the pH electrode all combine to produce a slower pH response compared to the conductivity change.

Removal of Micro Bubbles. Although no gas is formed in principle in the central channel, much gas is formed in the outer channels, especially at high operating currents. The central channel liquid thus becomes saturated with the electrolytic gas (which readily permeates the membranes). In the absence of significant backpressure, micro bubbles are formed in the detectors, the frequency of such bubbles predictably increasing with applied electrodialytic current. An example is shown in FIG. 12. We chose therefore to remove the gas from the central channel. Gas collection with a tubular porous membrane was first described 25 years ago and removal of gases by the reverse process shortly thereafter. We presently used a commercially available carbon dioxide removal device (CRD 200-4 mm, Dionex) immediately after the EBG, with both of the external jacket (regenerant) inlet/outlets of the CRD tied in common by a tee and connected to house vacuum (~180 Ton). While the CRD is designed for dissolved $CO_2$ removal, with vacuum applied, it can remove dissolved as well as physically present gas bubbles.

Results and Discussion

Figure 6:
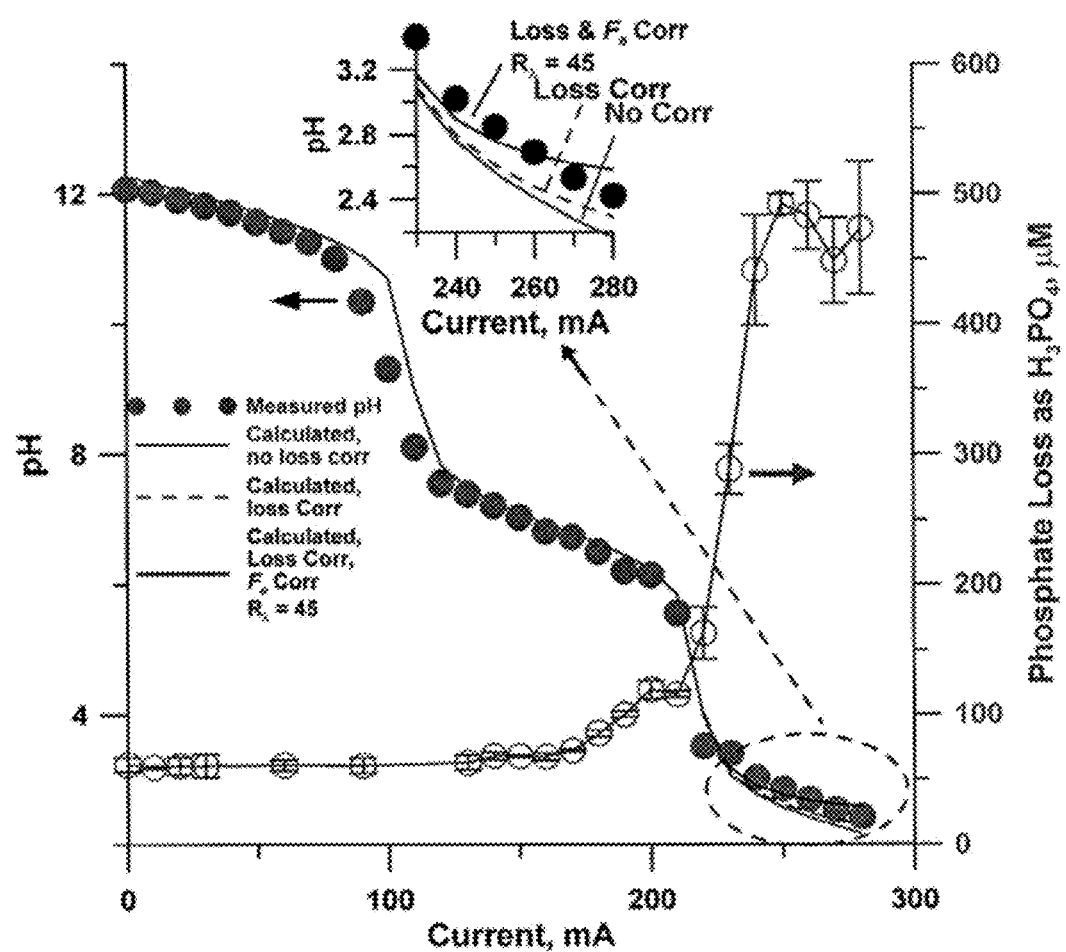
FIG. 6 is a pH as a function of applied current for 68 mM $Na_3PO_4$, CEM Suppressor (ASRS Ultra II (4-mm) 1 mL/min. The hollow circles (right ordinate) represent the concentration of the total phosphate lost through the membranes determined by IC analysis of outer channel effluent. The filled circles (left ordinate) represent the modified pH as a function of the current. The bottom right is shown in magnified form in the inset. The lines in the pH traces indicate computed values. See text for an explanation for the different computations.

Behavior of a Phosphate EBG. FIG. 6 shows the measured effluent pH (filled circles, left ordinate) for a CEM-suppressor system with 68 mM $Na_3PO_4$ as feed. The current vs. effluent pH profile exactly reflects the plot for a coulometric titration. Rather than a fixed solution volume, there is a constant flow rate; hence the appropriate control variable is current, rather than charge.

We also theoretically estimated the pH. Briefly, the following sequence was used: (a) estimate the ionic strength (I) of the solution, (b) compute individual ion activity coefficients from the Davies equation, (c) for each applicable constant, compute the applicable equilibrium constants in terms of concentrations, (d) express individual ionic concentrations based on these constants and $H^+$, (e) solve the relevant charge balance equation that contains all ions in solution for $H^+$ using Microsoft Excel Solver™, (f) compute all ion concentrations (g) cycle through a-f until convergence, (h) calculate the activity coefficient of $H^+$, $a_{H+}$, and activity-based pH. The theoretically calculated pH is represented as a solid gray line—it is slightly higher throughout the alkaline pH range compared to the measured pH values. This difference is ascribed to discrete collection and measurement in room air and consequent exposure to $CO_2$. On the other hand, at the low pH end, the theoretically computed pH values fall below the experimental values. While the negatively charged membranes effectively inhibit the loss of negative ions, there is no barrier towards the transport of a neutral molecule. There is a small but perceptible loss of $PO_4^{3-}$ as $H_3PO_4$ throughout the entire operating range. The amount lost was measured by IC and is shown in terms of the central channel concentration as hollow circles with error bars in FIG. 6 (right ordinate). Note that the highest loss (lowest pH) amounts to 0.7% of the total phosphate, not a significant amount. Also this occurs at the extreme end where it is not likely to be used as a buffer. In a suppressor, the two outer electrode channels are fluidically tied together; it is not possible to experimentally determine via which membrane the loss primarily occurs. However, logically it must be primarily through the anodic membrane, as $PO_4^{3-}$ is directed electrically to this membrane and the $H^+$ generated keeps the membrane in $H^+$-form. Therefore $H_3PO_4$ must be present as a thin layer at the internal surface of the membrane. The pattern of the loss is consistent with this view: the loss is low and essentially constant over a large current range and then starts increasing as $H_2PO_4^-$ begins to be titrated to $H_3PO_4$ in the final step and $H_3PO_4$ begins to be formed in significant concentration in the bulk solution. Incorporating this loss of $H_3PO_4$ into our computations (blue dashed line) make a difference only at the lowest pH end and brings the theoretical values closer to the measured values but still remain lower than the measured values.

Another factor to be considered at low pH is that the Faradaic efficiency ($F_e$) for $Na^+$ transport may not remain unity. In a CEM-based suppressor, current is carried by all cations, both $Na^+$ and $H^+$. When $[H^+]$ is no longer negligible relative to $[Na^+]$, the fraction of the current carried by $Na^+$ or $F_e$ will be given by:

$$F_e = \frac{\lambda_{Na+}[Na^+]}{(\lambda_{Na+}[Na^+]) + (\lambda_{H+}[H^+])} = \frac{1}{(1 + R_c R_\lambda)}. \quad (4)$$

where $\lambda_i$ is the equivalent conductance (proportional to ionic mobility) of ion i and $R_c$ and $R_\lambda$ are, respectively, the concentration ratio and the mobility ratios of $H^+$ and $Na^+$. The infinite dilution $R_\lambda$ value in solution, 6.98, is readily computed from known values for $\lambda_{Na+}$ and $\lambda_{H+}$. This provides at least a first approximation value to use in the computation; the exact $F_e$ value is also dependent on the selectivity coefficient (that governs membrane uptake) and relative transport speeds in the membrane. Available evidence suggests that in the membrane itself (which may be the limiting element), the mobility ratio of $H^+$ to $Na^+$ may be much greater than in free solution. In either case, the applicable form of eq 2 is:

$$\left(nC - F_e \frac{60i}{FQ}\right) + [H^+] - \frac{K_W}{[H^+]} - pC\sum_{p=1}^{n} \alpha_p = 0 \quad (5)$$

Using nonunity $F_e$ that results from a $R_\lambda$ value of 7 we calculate values at the low pH end that are numerically higher than the values where only $H_3PO_4$ loss is accounted for. But the difference is too small to be discerned in the scale of FIG. 6, even in the magnified inset view of the low pH end and hence was not plotted. However, if we keep increasing $R_\lambda$ values, agreement at the low end pH keeps getting better (note that this correction has no effect on pH≥4) but by the time $R_\lambda$ is made 45 (plotted as solid black line, see FIG. 6 inset), one is perceptibly overcorrecting relative to the lowest measured pH. We conclude that nonunity $F_e$ plays a role that is only of significance at the near-quantitative exchange end; this is of limited interest in buffer generation applications.

Figure 7:
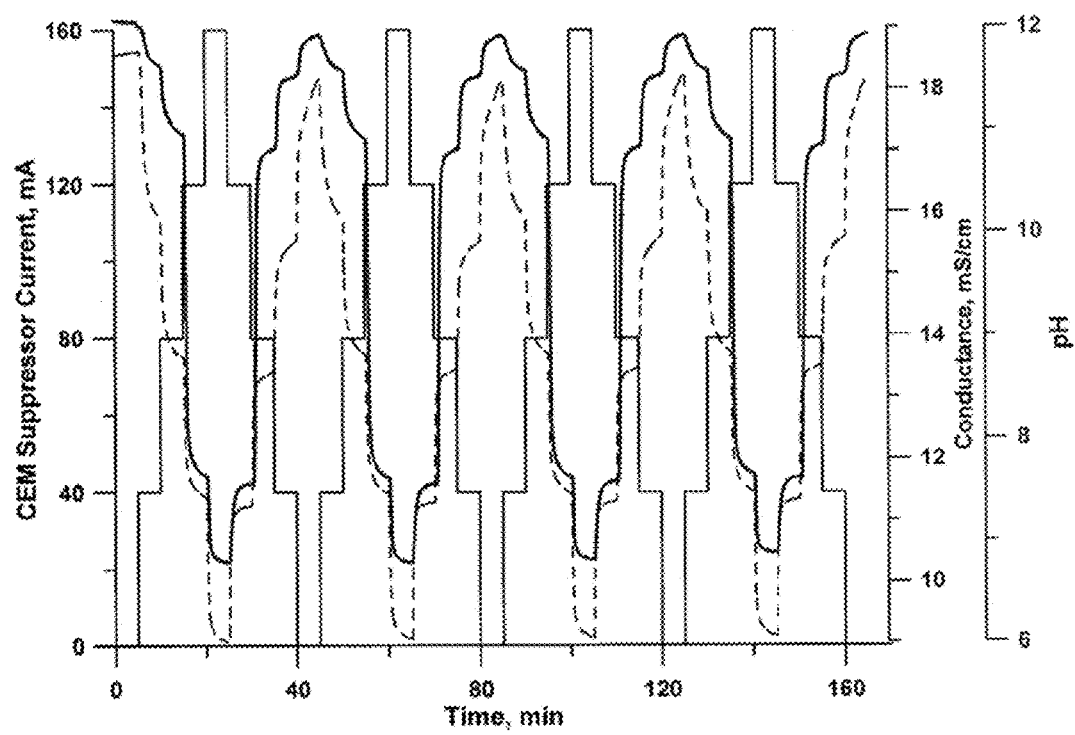
FIG. 7 is a step gradient response. Four cycles are shown for a $Na_3PO_4$ feed CEM suppressor system with an influent flow of 1 mL/min. Current steps have a staircase shape and are 0→40→80→120→160→120→80→40→0 mA, pH response is denoted with the thicker line, and conductance response is denoted with the dashed line.

Reproducibility and Response Time. FIG. 7 shows both conductivity and pH traces for a programmed current ascending and descending step gradient for the same phosphate system over four cycles. The system does exhibit some hysteresis. The membranes have significant ion exchange capacity and their ionic status depends on previous history and current flux. This creates a difference between the same current steps on ascending vs. descending profiles. However, absolute conductance values at either ascending or descending current steps are repeatable (0.30-0.43% rsd, average 0.36% rsd), the conductance values being slightly (0.14-0.38%) but perceptibly higher than descending current steps. Similar results are observed for pH: pH values for ascending steps being slightly (0.05-0.10 units) higher and the reproducibility within each type of step being within 0.005 to 0.05 pH unit. Response times to step changes in current were calculated from the conductivity detector response (as the pH electrode response is slower) and appears to depend on the status of the membrane. In ascending current steps, conductivity decreases and the 90-10% fall times for 0-40, 40-80, 80-120 and 120-160 mA steps were $2.54\pm0.27$, $2.07\pm0.09$, $1.60\pm0.07$ and $0.95\pm0.03$ min, while the 10-90% rise times for 160-120, 120-80, 80-40 and 40-0 mA steps were $0.68\pm0.06$, $0.92\pm0.15$, $2.12\pm0.05$ and $3.43\pm0.10$ min, respectively. The response is clearly faster at high currents when much of the membrane is in the more labile $H^+$-form and faster during descending current steps, which calls for less transport through the membrane. This suggests that the primary process that limits the response time is transport through the membrane. The response time may thus be faster where smaller current changes demand a small transport change, as in generating a pH gradient over a period of time. Detailed results are given in FIG. 14 and FIG. 15, Tables 1 and 2 for a current step of 2 mA (104⇔102 mA) for the same system. In this case, the respective 90-10% fall and 10-90% rise times for the conductance signals were lower and were more comparable to each other. They ranged from 0.61-1.41 and 0.72±1.85 min, respectively.

Figure 8:
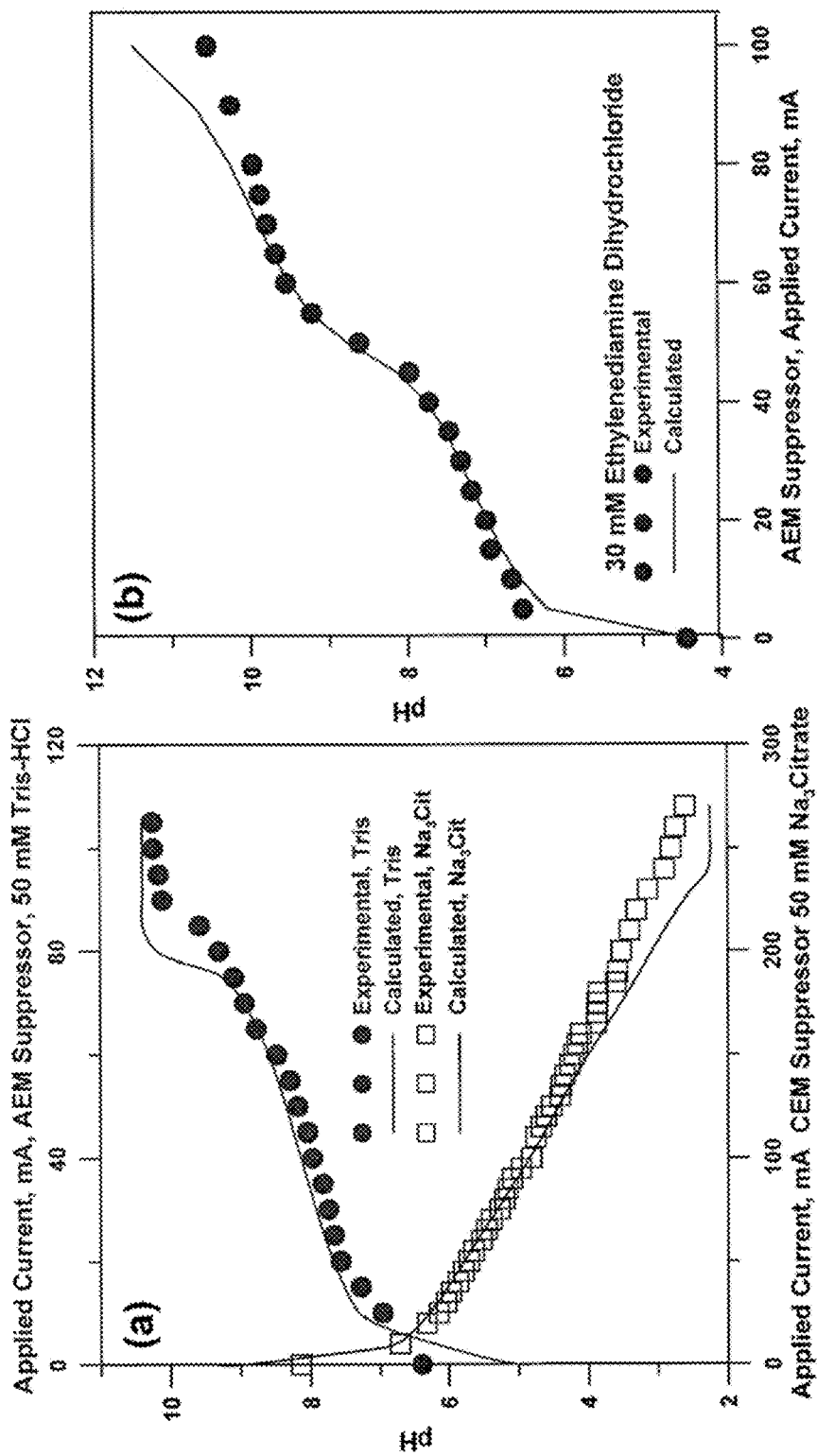
FIG. 8 is a pH as a function of drive current for (a) 50 mM Na3Citrate as the feed solution (ASRS Ultra II, 4-mm) and 50 mM Tris-HCl (CSRS Ultra, 4-mm), and (b) 30 mM ethylenediamine dihydrochloride (CSRS Ultra, 4-mm), all at 1.00 mL/min. The solid lines represent computed pH values, see text.

Other Buffers. FIG. 8a shows results for 50 mM trisodium citrate as the influent solution with the same CEM-based suppressor system. Since citric acid has three closely spaced $pK_a$ values (3.13, 4.75 and 6.40), individual titration steps are not observed; rather, a nearly linear gradient in pH (from 6.5 to 3) is seen. Citric acid is a substantially larger molecule than $H_3PO_4$. We have previously observed that under otherwise identical conditions, transport of citrate through an AEM is slower than phosphate. Since the loss of phosphate through the membrane was small and hardly affected the calculated pH, we did not measure citric acid loss and calculated pH without any loss assumption. It can be observed that the measured pH begins to significantly deviate from the computed values only below a pH of ~3.5.

Also in FIG. 8a is the behavior of a Tris-based buffer system with an AEM-based suppressor system. With a pKa of 8.1, it provides useful buffering in biologically important buffering range of 7-9. Loss of Tris as a free base was not measured. The computed pH of the initial solution is lower than the observed value, the commercial product that we assumed to be the pure hydrochloride likely contains a small amount of the free base. Thereafter the computed and observed values of pH agreed well up to pH ~9 (current ~200 mA). The point at which the theoretical and observed values begin to differ is where the last of the HCl is removed: the observed values show a much more gradual transition than the sharp change seen in theory. The calculation does not take into account any intrusion of dissolved $CO_2$ from the outer compartments to the center or during collection and measurement.

The two respective pKa values of the ethylenediammonium ion are 6.85 and 9.93. Both titration steps are observed, and the computed pH again agree with the observed pH over much of the useful buffering range. This establishes that the principle is equally applicable to multiprotic cationic (basic) buffer systems.

Electrodialytic Generation of a Large Range Linear pH Gradient. Leithe was the first to devise "linear buffers" for "single point titrations". The idea was to determine the concentration of a strong acid or strong base by simply adding an aliquot of it to a fixed volume of such a specially prepared buffer mixture and measuring the pH change. The buffer composition will be such that the pH change will be linearly related to the amount of the acid or the base added. Polyprotic acid-base buffering systems and mixtures thereof have been both theoretically and experimentally studied for the purpose; and at least two "polybuffers" based on polyampholytes that accomplish this over a limited pH range are commercially available (these are expensive: present cost is >$1/mL). Efforts to develop buffer compositions with multiple low MW species are given in a number of the papers cited in the introductory discussion on chromatofocusing. Instead of chromatography, the area of interest may be high-throughput $pK_a$ measurement. However, a common desired goal is a linear pH gradient. In reality what has been demonstrated is rather limited either in terms of an extended pH range or linearity. In flow applications, including chromatography, a further desired requirement must be to maintain a constant flow rate for a binary component mixture; otherwise a ternary or more complex gradient including a diluent will be needed. Box et al. describe mixing of two solutions, each consisting of six components, to achieve a linear gradient. Although data were not shown for the (linear) composition change vs. actual pH, between pH 3 and 11.6 the linear $r^2$ value between the computed and measured pH was stated to be 0.99.

Any buffer system generated by an EBG that generates a pH gradient with one or more buffering species is unlikely to produce a linear pH gradient that is driven by a linear current gradient, unless previous "linear buffer" compositions are adopted. Otherwise one ends up revisiting the same computation-composition experimentation-pH measurement-optimization steps common to previous efforts. A constant buffer capacity that accompanies a linear pH gradient is a great attribute but is not really needed for chromatography. What is needed is a buffer capacity sufficient to withstand a change in pH (within specified tolerance limits) when the analyte is added at any point in the gradient. For analytical scale chromatography this does not necessarily imply a large buffer capacity and is not a major limitation.

To achieve a linear pH gradient, let us pick several common buffering agents with $pK_a$ values spread across the range of interest. Phosphoric, citric and boric acids together provide pKa values of 2.10, 3.13, 4.75, 6.40, 7.20, 9.24 and 12.38. This potentially covers a large pH range of 2-12 with more of a gap between 9.24 and 12.38. This shortcoming can perhaps be partially addressed by increasing the borate concentration. The change in pH upon incremental removal of $K^+$ from a mixture containing 15 mM $K_3PO_4$, 15 mM $K_3$Citrate, 11.25 mM $K_2B_4O_7$ and sufficient KOH to adjust the pH to 12 (the last two components, equivalent to ~45 mM $KB(OH)_4$, provides 3× the buffer capacity of the final neutralization step of 15 mM $Na_3PO_4$) was computed (see Anal. Chem. 2012, 84, 67-75 and the associated Supporting Information). The same system was also experimentally studied with a staircase current gradient (t=0-120 min, i=0-300 mA; $\Delta t$=2 min, $\Delta i$=5 mA). From applying a current step to seeing the onset of the pH response was observed to be ~0.45 min. After accounting for this time lag, the pH data was averaged over 2 min increments and are plotted in FIG.

Figure 9:
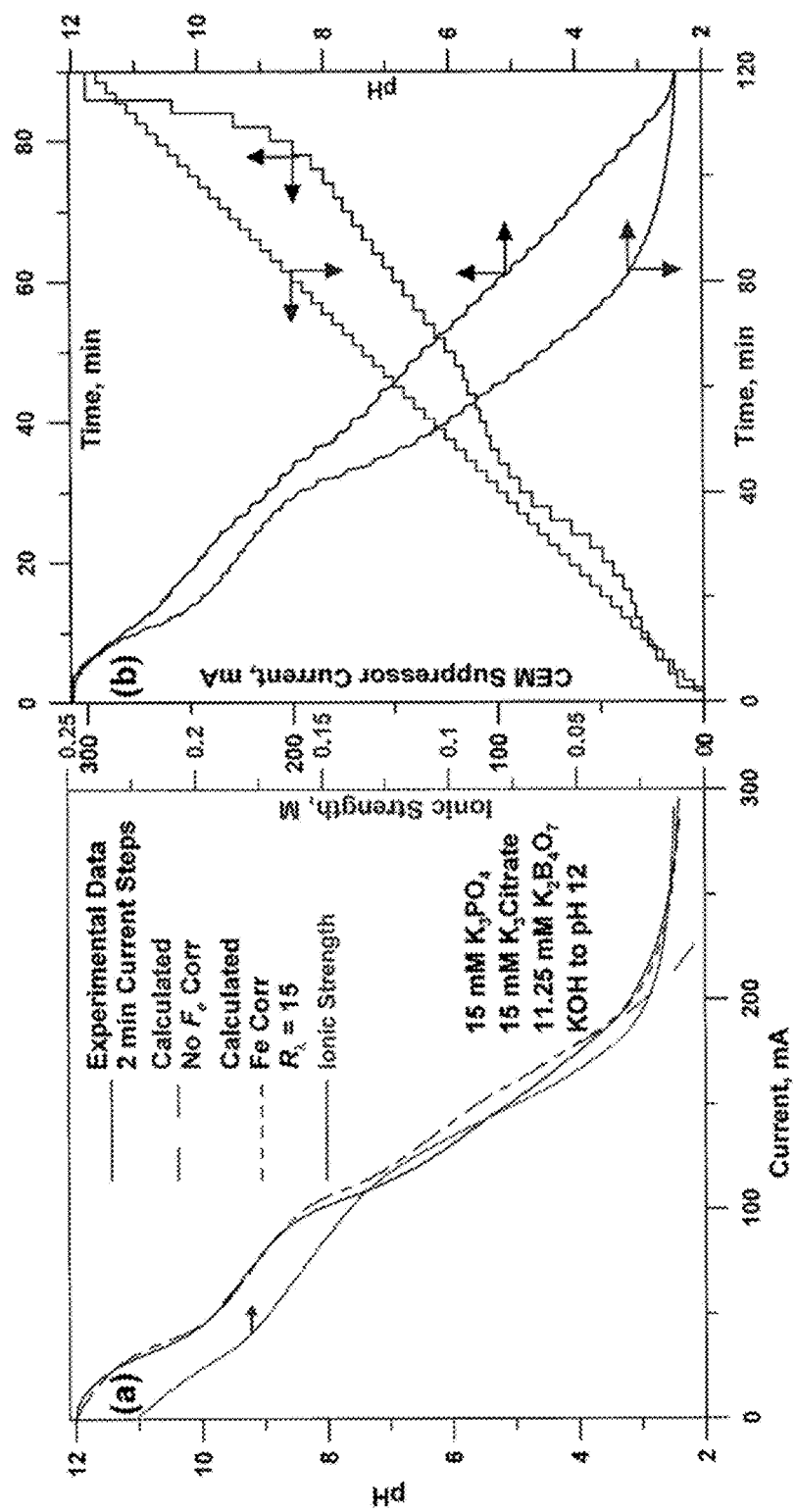
FIG. 9 is a CEM Suppressor (ASRS 4 mm), 1 mL/min; feed composition is in the inset. (a) Solid line (with no arrow pointing to the right ordinate) depicts experimental data obtained with 2 min current steps, the corresponding (time-lag corrected) 2 min averages for pH are plotted. The computed values are shown as dashed lines, the shorter dashed line takes non-unity Faradaic efficiency (Fe) due to current conduction by $H^+$ into account. See text. The line with an arrow pointing to the right ordinate shows the ionic strength (right ordinate). (b) red traces, bottom abscissa: 2 min uniform 5 mA current steps generate the pH profile which appears in 2 min averaged version in a; based on the observed profile a substantially linear gradient is generated using nonuniform current steps dictated by the observed current vs. pH values.
Figure 10:
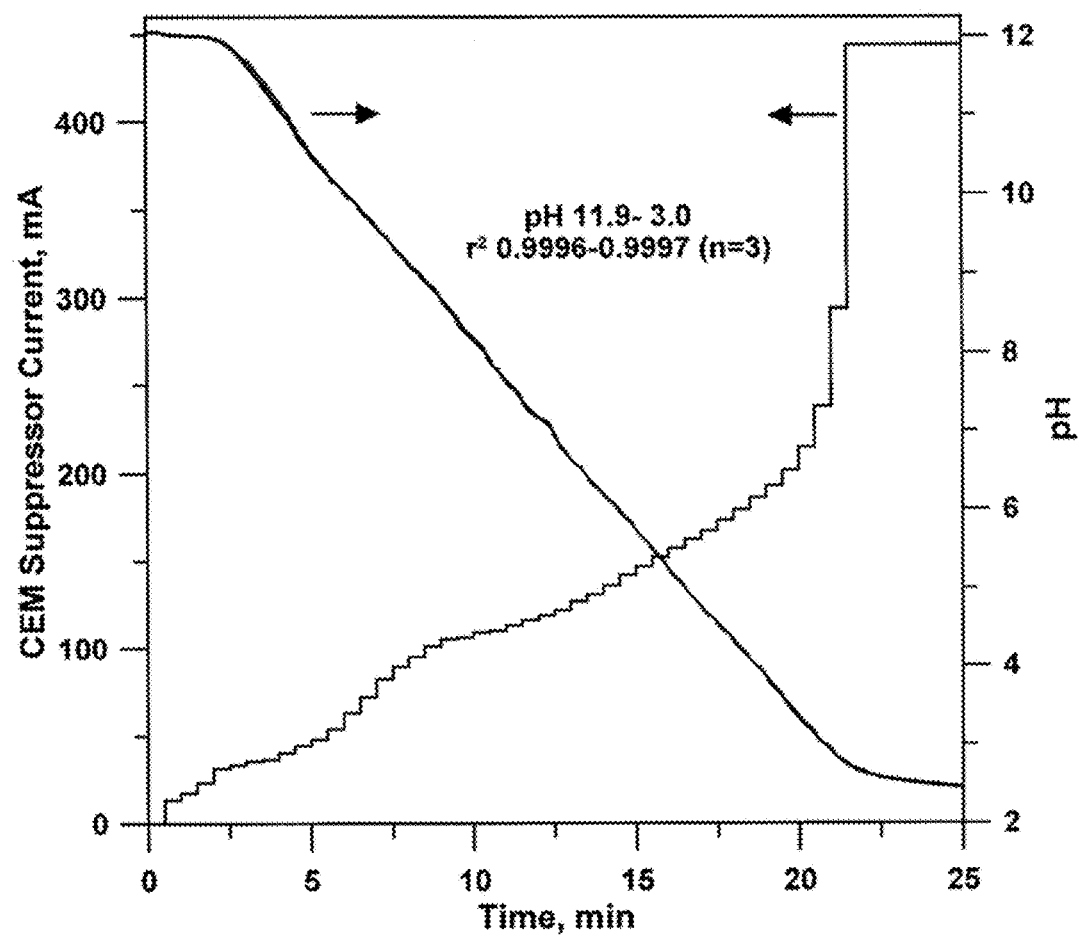
FIG. 10 is a three repeated 25 min linear pH gradient runs overlaid (right ordinate); the current program uses the left ordinate.

9a as the solid line. The computed data that (a) ignores the onset of nonunity $F_e$ and (b) incorporates nonunity $F_e$ with an $R_\lambda$ value of 15 (the dilute solution $R_\lambda$ value for $K^+$ and $H^+$ is ~4.76) are shown as dashed lines and differ only at the complete exchange end. Even for a relatively complex system, the relatively simple computation provides pH values close to measured values, useful at least for guidance. Knowing the behavior of the current vs. pH makes it simple to generate a substantially more linear pH gradient against time and also eliminate the wasted time near the end of the run where pH only decreases slowly. A single iteration of the original uniform current steps (red) to that suggested by the current-pH behavior produces the results in blue (FIG. 9b). Since the time steps are still obviously too long, reducing time steps to 0.5 min and taking this opportunity to do a further iteration of the current program to improve linearity produces the results in FIG. 6 which actually contains three overlaid traces of the generated pH profile indicating excellent reproducibility (among the triplicate set of 7500 time vs. pH points the maximum variance was 0.70%, average 0.20±0.14% RSD). The algorithm used for this iteration is discussed in the Supporting Information of Anal. Chem. 2012, 84, 67-75). While there are minor deviations that can still be improved on, our present hardware/software combination did not allow better than 1 mA resolution in current. This can be readily solved. Non-uniform time steps were possible but were eschewed for complexity. The linearity of the gradient generated with time exhibits an $r^2$ value of 0.9996, 0.9996 and 0.9997 from a pH range of 11.9 to 3. To manipulate the experimental pH to whatever desired form (linear, convex, concave), it must be obvious that it is much easier experimentally to reprogram a current profile than to alter solution compositions or mixing ratios between one or more components. In principle software that iteratively achieves any desired profile is relatively easily set up.

Maintaining a Relatively Constant Ionic Strength. FIG. 9a also shows the computed ionic strength profile that decreases continuously as the pH decreases; this may not be desirable. As long as the ionic strength provided by the buffering species concentration is significantly less than ionic strength provided by an indifferent salt, an approximately constant ionic strength can be maintained by the addition of a large amount of indifferent salt, e.g., NaCl. Aside from maintaining a near constant ionic strength, this has the added advantages that (a) $F_e$ will never have a nonunity value and (b) the buffer can have both cationic and anionic buffering components, e.g.; n-butylamine p$K_a$ 10.61, can be added to our previous phosphate-citrate-borate mixture to better fill the pK gap in this region. In the absence of large concentrations of NaCl, butylammonium (BuNH$_3^+$) ion would be lost from the system as a cationic charge carrier. But in the presence of a large excess of Na$^+$, the loss of the much less mobile (especially through the membrane) BuNH$_3^+$ will be expected to be insignificant.

Figure 11:
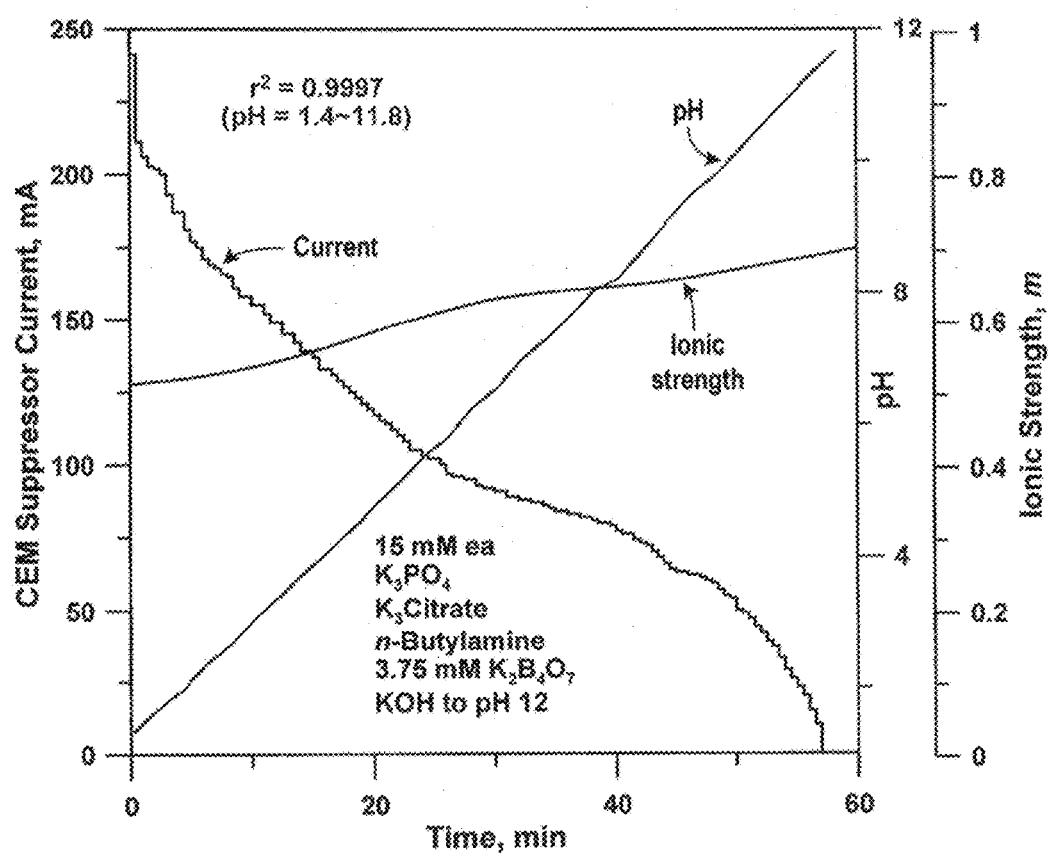
FIG. 11 is a four-component buffering mixture with an increasing linear pH gradient in the presence of large amounts of NaCl. Without the presence of the salt, the ionic strength will change by more than an order of magnitude (see FIG. 9a).

Thus, 15 mmol/L each of K$_3$PO$_4$, K$_3$Citrate, and BuNH$_2$ and 3.75 mmol/L of K$_2$B$_4$O$_7$ per liter of water were dissolved and added 0.500 mol NaCl to this solution. Computations were made using the known mean ionic activity coefficient of NaCl for a 0.5 m solution (0.680) and single ion activity coefficients were calculated therefrom noting charge and size dependence. Both computed and experimental results are shown in FIG. 11. Note that since $F_e$ remains unity throughout, the buffer capacity at any point is essentially the reciprocal of the pH vs the drive current plot. Herein descending current gradient was used to demonstrate the capability of a CEM-based suppressor to generate a temporally increasing pH profile which has a relatively minor accompanying change in ionic strength.

In summary, the principles and practice of generating pH buffers electrodialytically were demonstrated with commonly available suppressors for IC. While present suppressors will not support pressures high enough to conveniently locate the device on the high pressure side of a pump, ion exchange bead based devices that tolerate much higher pressures have already been described. Such devices can be readily constructed in an array format. With a ternary gradient system, an organic solvent gradient can be incorporated without a change in buffer ion concentration. To generate an additional gradient in ionic strength/salt beyond that resulting from pH change, a further pumping channel will be needed to add more or less salt.

It is also clear that suppressors can be used as flow-through coulometric ion removal devices. This property can be readily exploited as a process titrator, especially in conjunction with rapid triangular wave current sweeps as previously reported. For sample streams that can flow through the suppressor, an AEM-based suppressor can be used to remove anions, introduce OH$^-$ and titrate an acidic stream while a CEM based suppressor can be used to remove cations, introduce H$^+$ and titrate a base. For streams that are not compatible to directly flow through the suppressor, salt solutions flowing through a CEM/AEM suppressor can generate the titrant acid/base, respectively, in current-controlled mode to be added to the sample stream.

Even in a purely aqueous system, it is not possible to independently control both pH and ionic strength with a suppressor based EBG, especially when the ionic strength is controlled by the buffering species.

The present invention provides, inter alia, novel buffer generations and methods of using these generators. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

The present invention is described as a device, a system and as methods, each of which is exemplified by the description of exemplary components and exemplary arrangements and connections of these components. The embodiments set forth herein are for the purpose of illustration and it will be apparent to one of ordinary skill in the art that any of the features of the devices, systems and methods described herein can be combined with any single feature or combination of features of any other embodiment set forth herein.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. An electrodialytic method for generating a modified buffer solution, said method comprising:
   (a) flowing a first buffer solution including cations and anions to a modified-buffer generation flow channel;

(b) flowing an aqueous solution including cations and anions to a source channel separated from said modified-buffer generation flow channel by a first ion exchange barrier, and capable of exchanging cations or anions, but not both, and blocking bulk liquid flow, in which a first electrode is disposed in said source channel;

(c) flowing a deionized water stream to a receiving channel separated from said modified-buffer generation flow channel by a second ion exchange barrier, and capable of exchanging cations or anions, but not both, and blocking bulk liquid flow, in which a second electrode is disposed in said receiving channel, wherein said first ion exchange barrier and said second ion exchange barrier are anion exchange barriers, or said first ion exchange barrier and said second ion exchange barrier are cation exchange barriers; and (d) passing a current between said first and second electrodes across said modified-buffer generation flow channel to cause cations or anions, but not both, of said source channel to be transported across said first ion exchange barrier to said modified-buffer generation flow channel, and to cause cations or anions, but not both, of said modified-buffer generation flow channel to be transported across said second ion exchange barrier to said receiving channel to generate a modified buffer solution which exits from said modified-buffer generation flow channel;

wherein said modified-buffer generation flow channel is fluidically coupled to a chromatography column upstream of said chromatography column.

2. The method of claim 1, further comprising:
outputting said modified buffer solution from said modified-buffer generation flow channel with a modified buffer concentration, in which a magnitude of said current is proportional to a change in a concentration of said flowed buffer solution.

3. The method of claim 1, further comprising injecting a sample with analyte ions to be separated into said exiting modified buffer and separating said analyte ions on said chromatography column; said buffer solution flowing to said modified-buffer generation flow channel not being previously generated by an electrodialytic eluent generator.

4. The method of claim 1, wherein said first and second ion exchange barriers are anion exchange barriers.

5. The method of claim 1, wherein said first and second ion exchange barriers are cation exchange barriers.

* * * * *